(12) United States Patent
Sakumoto et al.

(10) Patent No.: US 11,610,430 B2
(45) Date of Patent: Mar. 21, 2023

(54) INFORMATION PROCESSING APPARATUS, WEARABLE DEVICE, INFORMATION PROCESSING METHOD, AND PROGRAM

(71) Applicant: SONY CORPORATION, Tokyo (JP)

(72) Inventors: Koichi Sakumoto, Tokyo (JP); Kiyoshi Yoshikawa, Saitama (JP); Naoto Tsuboi, Saitama (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/056,594

(22) PCT Filed: May 9, 2019

(86) PCT No.: PCT/JP2019/018528
§ 371 (c)(1),
(2) Date: Nov. 18, 2020

(87) PCT Pub. No.: WO2019/244497
PCT Pub. Date: Dec. 26, 2019

(65) Prior Publication Data
US 2021/0209333 A1 Jul. 8, 2021

(30) Foreign Application Priority Data

Jun. 19, 2018 (JP) .............................. JP2018-115760

(51) Int. Cl.
*G06V 40/12* (2022.01)
*G06T 7/73* (2017.01)
(Continued)

(52) U.S. Cl.
CPC ............ *G06V 40/1353* (2022.01); *G06T 7/73* (2017.01); *G06V 10/30* (2022.01); *G06V 40/1365* (2022.01); *G06V 40/15* (2022.01)

(58) Field of Classification Search
CPC .. G06K 9/00073; G06K 9/00087; G06K 9/40; G06K 9/00006; G06K 2009/00939;
(Continued)

(56) References Cited

U.S. PATENT DOCUMENTS

2004/0114784 A1* 6/2004 Fujii .................. G06K 9/00026
382/124
2006/0228006 A1 10/2006 Matsumoto et al.
(Continued)

FOREIGN PATENT DOCUMENTS

JP 2003-044856 A 2/2003
JP 2004-164170 A 6/2004
(Continued)

OTHER PUBLICATIONS

Surekha Dholay et al., Finger Print Recognition using Image Processing, Third International Conference on Digital Image Processing (ICDIP 2011), Jun. 2011, pp. 1-7, SPIE.
(Continued)

*Primary Examiner* — Edward F Urban
*Assistant Examiner* — Wassim Mahrouka
(74) *Attorney, Agent, or Firm* — Paratus Law Group, PLLC

(57) ABSTRACT

An information processing apparatus, including: a feature point detecting unit configured to detect a feature point from an image including biological information obtained via a sensor unit; and a feature value extracting unit configured to extract a feature value that characterizes the feature point based on a peripheral image including the feature point.

20 Claims, 27 Drawing Sheets

(51) Int. Cl.
*G06V 10/30* (2022.01)
*G06V 40/10* (2022.01)

(58) Field of Classification Search
CPC ....... G06T 7/73; G06F 21/32; G06F 3/04182;
G06F 3/017; G06F 3/014; G04G 21/025;
A61B 5/6824; A61B 5/681; A61B 5/1172
See application file for complete search history.

(56) References Cited

U.S. PATENT DOCUMENTS

| | | | | |
|---|---|---|---|---|
| 2012/0020535 | A1* | 1/2012 | Liachenko | G06K 9/00073 |
| | | | | 382/125 |
| 2016/0042219 | A1* | 2/2016 | Bae | G06K 9/00013 |
| | | | | 382/124 |
| 2016/0055367 | A1* | 2/2016 | Hara | G06K 9/033 |
| | | | | 382/125 |
| 2018/0005005 | A1* | 1/2018 | He | G06F 3/0418 |
| 2018/0101713 | A1* | 4/2018 | Chang | G06K 9/0002 |
| 2019/0384904 | A1* | 12/2019 | Fukuda | G06F 7/582 |

FOREIGN PATENT DOCUMENTS

| | | | | |
|---|---|---|---|---|
| JP | 3597148 | B2 * | 12/2004 | ......... G06K 9/00067 |
| JP | 2009-110452 | A | 5/2009 | |
| JP | 2012-248047 | A | 12/2012 | |
| JP | 5712746 | B2 | 5/2015 | |
| WO | WO 2015/100371 | A1 | 7/2015 | |
| WO | WO-2017038695 | A1 * | 3/2017 | ........... A61B 5/1172 |

OTHER PUBLICATIONS

A.R. Roddy et al., Fingerprint Feature Processing Techniques and Poroscopy, Intelligent Biometric Techniques in Fingerprint and Face Recognition, Oct. 1, 1999, pp. 37-105, CRC Press LLC.

* cited by examiner

INFORMATION PROCESSING APPARATUS, WEARABLE DEVICE, INFORMATION PROCESSING METHOD, AND PROGRAM

CROSS REFERENCE TO PRIOR APPLICATION

This application is a National Stage Patent Application of PCT International Patent Application No. PCT/JP2019/018528 (filed on May 9, 2019) under 35 U.S.C. § 371, which claims priority to Japanese Patent Application No. 2018-115760 (filed on Jun. 19, 2018), which are all hereby incorporated by reference in their entirety.

TECHNICAL FIELD

The present disclosure relates to an information processing apparatus, a wearable device, an information processing method, and a program.

BACKGROUND ART

Conventionally, apparatuses that perform authentication using biological information such as a fingerprint are known (for example, refer to PTL 1 below).

CITATION LIST

Patent Literature

[PTL 1]
JP 5712746 B

SUMMARY

Technical Problem

In such fields, the use of appropriate information for performing accurate authentication is desired.

An object of the present disclosure is to provide an information processing apparatus, a wearable device, an information processing method, and a program which acquire appropriate information for performing accurate authentication.

Solution to Problem

For example, the present disclosure is
an information processing apparatus including:
a feature point detecting unit configured to detect a feature point from an image including biological information obtained via a sensor unit; and
a feature value extracting unit configured to extract a feature value that characterizes the feature point based on a peripheral image including the feature point.

For example, the present disclosure is
a wearable device including:
a display with which a fingerprint comes into contact;
a sensor unit configured to acquire an image including a fingerprint;
a light-emitting unit configured to emit light at least during acquisition of the image:
a feature point detecting unit configured to detect a feature point from a fingerprint image obtained via the sensor unit; and
a feature value extracting unit configured to extract a feature value that characterizes the feature point based on a peripheral image including the feature point.

For example, the present disclosure is
an information processing method including:
by a feature point detecting unit, detecting a feature point from an image including biological information obtained via a sensor unit; and
by a feature value extracting unit, extracting a feature value that characterizes the feature point based on a peripheral image including the feature point.

For example, the present disclosure is
a program that causes a computer to execute an information processing method including:
by a feature point detecting unit, detecting a feature point from an image including biological information obtained via a sensor unit; and
by a feature value extracting unit, extracting a feature value that characterizes the feature point based on a peripheral image including the feature point.

Advantageous Effects of Invention

According to at least one embodiment of the present disclosure, appropriate information for performing accurate authentication can be acquired. It should be noted that the advantageous effect described above is not necessarily restrictive and any of the advantageous effects described in the present disclosure may apply. In addition, it is to be understood that contents of the present disclosure are not to be interpreted in a limited manner according to the exemplified advantageous effects.

DESCRIPTION OF EMBODIMENTS

Hereinafter, embodiments and the like of the present disclosure will be described with reference to the drawings. The descriptions will be given in the following order.

<First Embodiment>
<Second Embodiment>
<Modifications>

It is to be understood that the embodiments and the like to be described below are preferable specific examples of the present disclosure and that contents of the present disclosure are not to be limited to the embodiments and the like.

First Embodiment

[Wristband-Type Electronic Device]

(Example of External Appearance of Wristband-Type Electronic Device)

Figure 1:
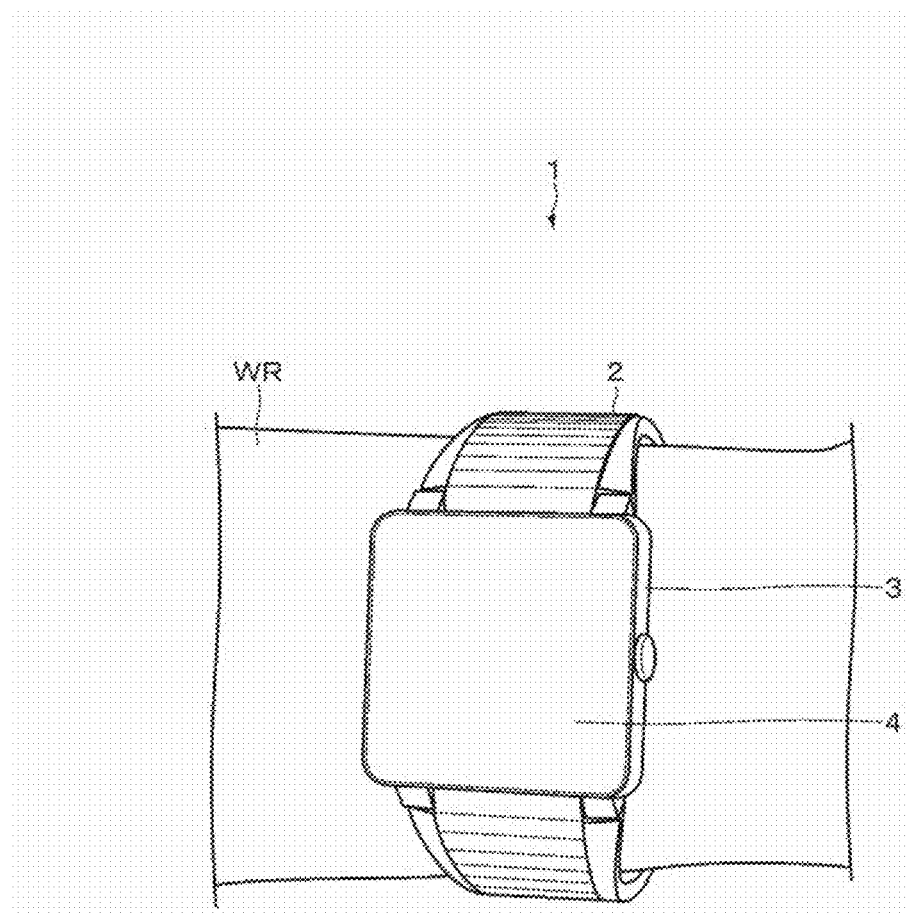
FIG. 1 is a diagram showing an example of an external appearance of a wristband-type electronic device according to an embodiment.

A first embodiment will now be described. The first embodiment represents an example in which the present disclosure is applied to an example of an information processing apparatus or, more specifically, to a wristband-type electronic device that represents an example of a wearable device. FIG. 1 shows an example of an external appearance of a wristband-type electronic device (a wristband-type electronic device 1) according to the first embodiment.

As shown in FIG. 1, for example, the wristband-type electronic device 1 is used just like a wrist watch. More specifically, the wristband-type electronic device 1 has a band part 2 to be wrapped around a wrist WR of a user and a main body unit 3. The main body unit 3 has a display 4. Although details will be described later, the wristband-type electronic device 1 according to the embodiment enables biometric authentication using fingerprint information of a fingertip to be performed by causing the fingertip to come into contact with the display 4.

(Example of Internal Structure of Wristband-Type Electronic Device)

Figure 2:
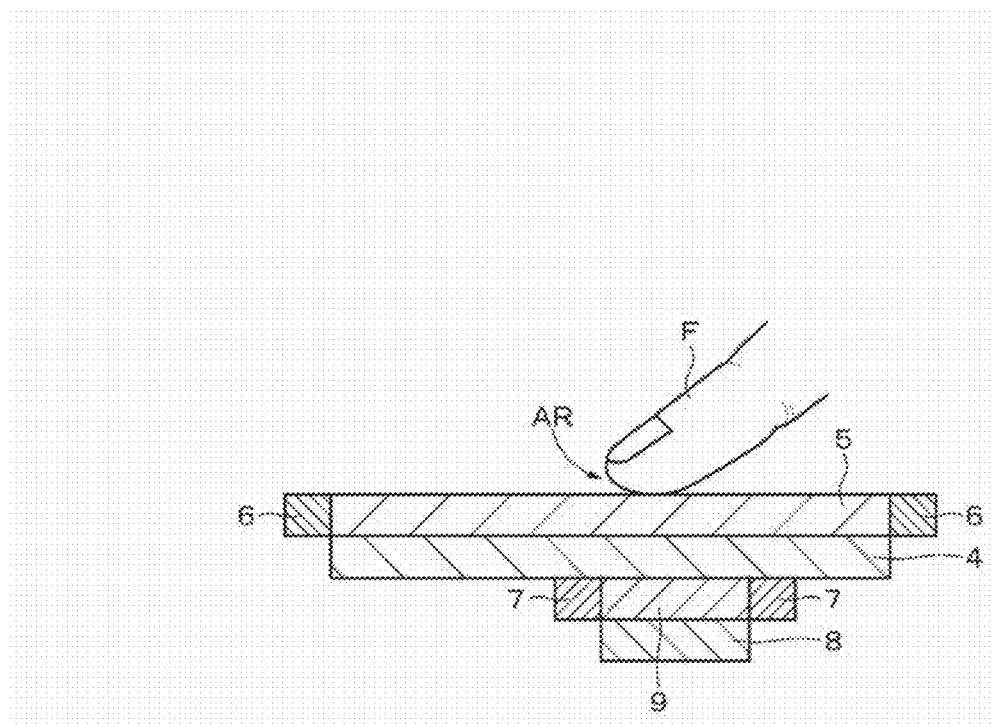
FIG. 2 is a diagram showing an example of an internal structure of the wristband-type electronic device according to the embodiment.

FIG. 2 is a partial sectional view for explaining an example of an internal structure of the main body unit 3 of the wristband-type electronic device 1. For example, the main body unit 3 of the wristband-type electronic device 1 has the display 4 described above, a light guide plate 5, a light-emitting unit 6, a touch sensor unit 7, an imaging element 8 that represents an example of the sensor unit, and a lens unit 9.

Generally, as shown in FIG. 2, a contact operation by a fingertip F is performed with respect to the display 4 and the presence or an absence of contact is detected by the touch sensor unit 7. The main body unit 3 of the wristband-type electronic device 1 has a structure in which the light guide plate 5, the display 4, the lens unit 9, and the imaging element 8 are stacked in this order from a near side to a far side as viewed in an operation direction. The contact with respect to the display 4 may include not only a direct contact with respect to the display 4 but also indirect contact via another member (for example, the light guide plate 5). In addition, the contact with respect to the display 4 may include not only the fingertip F coming into contact with the display 4 but also bringing the fingertip F close enough to the display 4 so that a fingerprint image is obtained.

Hereinafter, each component will be described. The display 4 is constituted by a liquid crystal LCD (Liquid Crystal Display), an OLED (Organic Light Emitting Diode), or the like. For example, the light guide plate 5 is a light-transmitting member that guides light from the light-emitting unit 6 to an area AR that is a position with which the fingertip F is to come into contact. The light guide plate 5 is not limited to being transparent and any light guide plate may be used as long as enough light is transmitted to enable a fingerprint of the fingertip F to be photographed by the imaging element 8.

The light-emitting unit 6 is constituted by an LED (Light Emitting Diode) or the like and is provided in at least a part of a periphery of the light guide plate 5. The area AR is an area that includes a position corresponding to the imaging element 8 or, more specifically, a position at least corresponding to a range of photography by the imaging element 8. The light-emitting unit 6 provides light necessary for photography by being lighted when photographing, for example, a fingerprint.

The touch sensor unit 7 is a sensor that detects contact by the fingertip F with respect to the display 4. For example, a electrostatic capacitance system touch sensor is applied as the touch sensor unit 7. Alternatively, a touch sensor of another system such as a resistive film system may be applied as the touch sensor unit 7. While the touch sensor unit 7 is locally provided at a position near a lower part of the area AR in FIG. 2, the touch sensor unit 7 may be provided across an approximately entire lower side of the display 4.

The imaging element 8 is constituted by a CCD (Charge Coupled Device), a CMOS (Complementary Metal Oxide Semiconductor), or the like. The imaging element 8 photoelectrically converts subject light incident via the lens unit 9 (reflected light from an object in contact with the display 4) into a charge amount. Various types of processing in subsequent stages are performed with respect to an image signal obtained via the imaging element 8. The lens unit 9 is constituted by lenses (microlenses) provided at intervals of one per every several ten to several hundred pixels of the imaging element 8.

Figure 3:
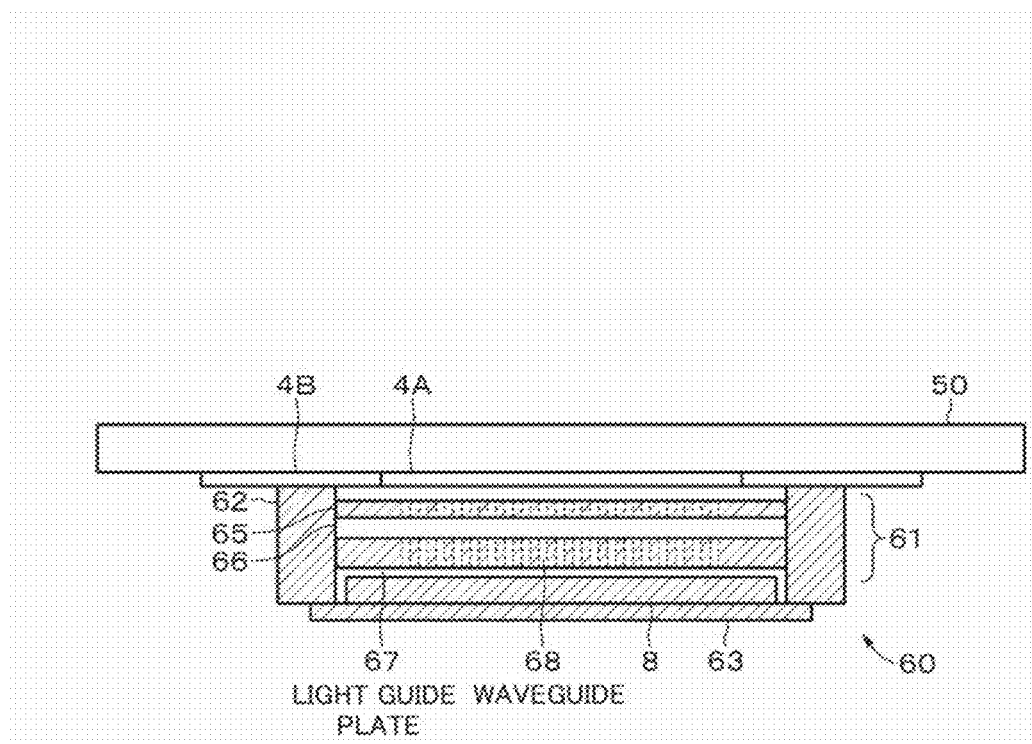
FIG. 3 is a diagram showing a more specific example of the internal structure of the wristband-type electronic device.

FIG. 3 is a diagram showing a more specific example of the internal structure of the wristband-type electronic device 1. In the example described below, the display 4 will be described as a transparent panel unit having a plurality of transparent light-emitting elements such as transparent organic EL elements or quantum dot light-emitting elements.

As shown in FIG. 3, the display 4 has an effective area 4A and an outer frame portion 4B. The display 4 functions as a display panel that displays an image in the effective area 4A due to light emitted by the plurality of transparent light-emitting elements. The transparent light-emitting elements are arranged in the effective area 4A in, for example, a matrix pattern. In addition, the display 4 functions as a touch sensor that detects a touch state by an object such as a finger based on, for example, a value of capacitance between a plurality of wirings for the light-emitting elements. As shown in FIG. 3, a cover glass 50 is provided on an upper surface (an operation side) of the display 4 and an imaging unit 60 including the imaging element 8 is arranged below a partial area of the display 4.

The imaging unit 60 is arranged below a partial area of the display 4. The imaging unit 60 has a function of capturing, via the display 4, an image of an object that comes into contact or approaches the partial area of the display 4. The object to be captured by the imaging unit 60 may be, for example, a part of a living organism. The imaging unit 60 may function as a biometric authentication device that performs biometric authentication of the part of the living organism based on a captured image of the part of the living organism having been obtained by capturing the part of the living organism. For example, a fingerprint sensor may be constructed based on the function of the imaging unit 60 as a biometric authentication device.

As shown in FIG. 3, the imaging unit 60 has a microlens array module 61, an imaging unit outer frame 62, the imaging element 8 described above, and a substrate 63. The microlens array module 61 is arranged inside the effective area 4A of the display 4 as viewed from an upper side. The imaging element 8 is arranged on the substrate 63.

The microlens array module 61 is arranged between the imaging element 8 and the effective area 4A of the display 4. The microlens array module 61 has, in order from the upper side, a cover glass-light guide plate 65, a microlens array 66, and a light guide plate 67.

The microlens array 66 has a plurality of microlenses that are arranged in a matrix pattern. Using each of the plurality of microlenses, the microlens array 66 collects object light from an object such as a finger toward the imaging element 8.

The cover glass-light guide plate 65 has a role of protecting a surface of the microlens array 66. In addition, the cover glass-light guide plate 65 has a role of guiding object light having passed through the effective area 4A of the display 4 to each of the plurality of microlenses. The cover glass-light guide plate 65 has a plurality of waveguides of which each is provided at a position corresponding to each of the plurality of microlenses.

As shown in FIG. 3, the light guide plate 67 has a plurality of waveguides 68. Each of the plurality of waveguides 68 is provided at a position corresponding to each of the plurality of microlenses and is configured to guide light collected by each of the plurality of microlenses to the imaging element 8.

(Example of Circuit Configuration of Wristband-Type Electronic Device)

Figure 4:
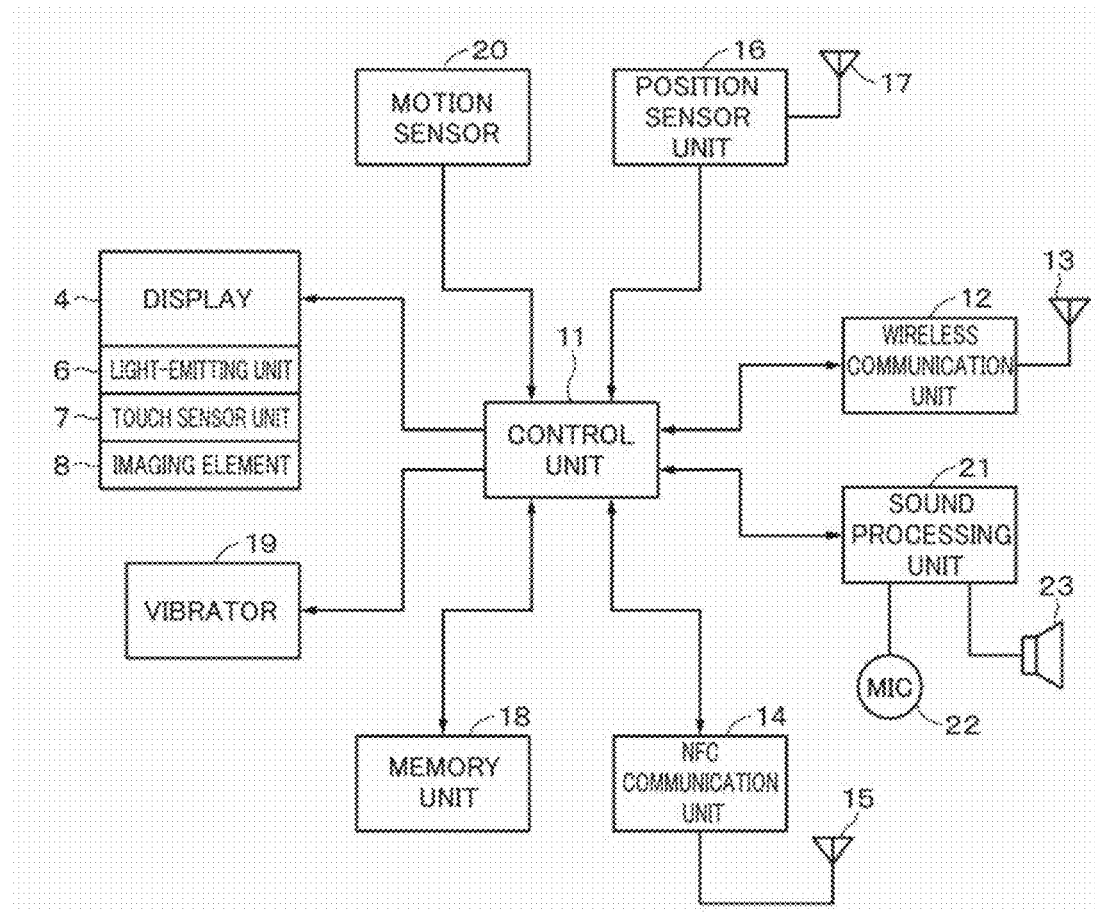
FIG. 4 is a block diagram showing an example of a circuit configuration of the wristband-type electronic device according to the embodiment.

FIG. 4 is a block diagram showing an example of a circuit configuration and the like of the wristband-type electronic device 1. In addition to the display 4, the touch sensor unit 7, the imaging element 8, and the like described above, the wristband-type electronic device 1 has, for example, a control unit 11, a wireless communication unit 12, an antenna 13 to be connected to the wireless communication unit 12, an NFC (Near Field Communication) communication unit 14, an antenna 15 to be connected to the NFC communication unit 14, a position sensor unit 16, an antenna 17 to be connected to the position sensor unit 16, a memory unit 18, a vibrator 19, a motion sensor 20, a sound processing unit 21, a microphone 22, and a speaker 23.

The control unit 11 is constituted by a CPU (Central Processing Unit) or the like and controls the respective units of the wristband-type electronic device 1. For example, the control unit 11 performs various types of image processing on a fingerprint image of the fingertip F photographed by the imaging element 8 and performs fingerprint authentication based on an image (a fingerprint image) of a fingerprint that represents a type of biological information.

The wireless communication unit 12 performs short-range wireless communication with other terminals based on, for example, the Bluetooth (registered trademark) standard. The wireless communication unit 12 performs modulation/demodulation processing, error correction processing, and the like in correspondence with, for example, the Bluetooth (registered trademark) standard.

The NFC communication unit 14 performs wireless communication with a proximal reader/writer based on the NFC standard. Although not illustrated, power is supplied to each unit of the wristband-type electronic device 1 from a battery such as a lithium-ion secondary battery. The battery may be configured to be wirelessly charged based on the NFC standard.

The position sensor unit 16 is a positioning unit that measures a present position using, for example, a system referred to as the GNSS (Global Navigation Satellite System). Data obtained by the wireless communication unit 12, the NFC communication unit 14, and the position sensor unit 16 is supplied to the control unit 11. In addition, the control unit 11 executes control based on the supplied data.

The memory unit 18 collectively refers to a ROM (Read Only Memory) that stores a program to be executed by the control unit 11, a RAM (Random Access Memory) to be used as a work memory when the control unit 11 executes the program, a non-volatile memory for data storage, and the like. The memory unit 18 stores a feature value (hereinafter, referred to as a registered feature value when appropriate) of a fingerprint of an authorized user to be used for fingerprint authentication. For example, the registered feature value is initially registered when using the wristband-type electronic device 1 for the first time.

The vibrator 19 is a member that vibrates, for example, the main body unit 3 of the wristband-type electronic device 1. A reception of a phone call, a reception of an e-mail, and the like are notified by the vibration of the main body unit 3 caused by the vibrator 19.

The motion sensor 20 detects a motion of the user wearing the wristband-type electronic device 1. As the motion sensor 20, an acceleration sensor, a gyroscope sensor, an electronic compass, an atmospheric pressure sensor, a biosensor that detects blood pressure, pulse, or the like is used. In addition, a pressure sensor or the like for detecting whether or not the user is wearing the wristband-type electronic device 1 may be provided on a reverse side (a side facing the wrist) of the band part 2 or the main body unit 3.

The microphone 22 and the speaker 23 are connected to the sound processing unit 21, and the sound processing unit 21 processes a call with a person being connected by wireless communication performed by the wireless communication unit 12. In addition, the sound processing unit 21 can also perform processing for sound input operations.

Since the display 4, the touch sensor unit 7, and the like have already been described above, redundant descriptions will be omitted.

This concludes the description of a configuration example of the wristband-type electronic device 1. It is needless to say that the wristband-type electronic device 1 is not limited to the configuration example described above and may have a configuration in which a part of the components of the wristband-type electronic device 1 described above have been omitted or a configuration in which other components have been added.

[Control Unit]

Figure 5:
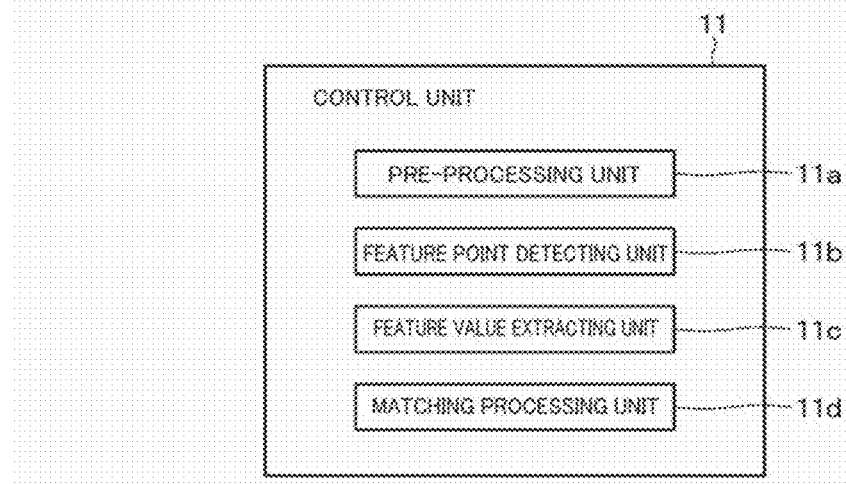
FIG. 5 is a functional block diagram for explaining function examples of a control unit according to the embodiment.

FIG. 5 is a functional block diagram for explaining an example of functions of the control unit 11. The control unit 11 has a pre-processing unit 11a, a feature point detecting unit 11b, a feature value extracting unit 11c, and a matching processing unit 11d.

The pre-processing unit 11a performs various types of correction processing with respect to a fingerprint image to be input. Details of processing to be performed by the pre-processing unit 11a will be described later.

Figure 6:
FIG. 6 is a diagram for explaining a feature point of a fingerprint.

The feature point detecting unit 11b detects a feature point of a fingerprint from an image including the fingerprint by applying known methods. A feature point of a fingerprint is, for example, as shown in FIG. 6, an ending or a bifurcation in a pattern drawn by a fingerprint line of the fingerprint or an intersection or an isolated point of the fingerprint line as will be described later, and is a characteristic location necessary for collating the fingerprint. While a fingerprint line will be described in the present embodiment as a ridge line of a fingerprint, a fingerprint line need only be at least one of a ridge line and a valley line of the fingerprint.

The feature value extracting unit 11e extracts a feature value that characterizes each feature point detected by the feature point detecting unit 11b. Examples of a feature value include a position of the feature point and an orientation of a feature line (for example, a relative orientation (vector) with respect to a prescribed direction that is defined by a ridge line). In the present embodiment, the feature value extracting unit 11c extracts a feature value of a feature point based on a peripheral image that includes the feature point. For example, while an image centered on the feature point, cut out in a size of 3 mm×3 mm, and normalized by angle is applied as the peripheral image, the peripheral image is not limited thereto. However, it should be noted that, as an effect of extracting a feature value after normalization by angle, even if a photographed orientation of a finger differs between during registration and during collation, normalizing an angle of the feature point produces an effect of making an extracted feature value less susceptible to change or, in other words, improving robustness with respect to an angle in which the finger is placed. Using the peripheral image enables information on a periphery of a feature point to be included in a feature value. For example, when a sweat gland is present in the periphery of the feature point, a relative position of the sweat gland with respect to the feature point can be adopted as a feature value of the feature point. In this manner, in the present embodiment, at least one of a position of a feature point, an orientation of a feature point, and a position of a sweat gland is used as a feature value. In particular, when using a high-resolution image of 1000 ppi or higher, since an individual can be sufficiently identified even with a small number of feature points (for example, one or two), an embodiment according to the present disclosure may be described a method suitable for fingerprint collation in a small area which does not necessarily require fingerprint photography of a wide range of a finger.

The matching processing unit 11d performs matching processing for collating a feature value extracted by the feature value extracting unit 11c and the registered feature value having been registered in advance and outputs a collated score that represents a result of the matching processing. When the collated score is equal to or higher than a threshold, fingerprint authentication is valid or, in other words, a determination of an authorized user is made. Conversely, when the collated score is lower than the threshold, the fingerprint authentication is invalid. A result of the matching processing may be notified to the user by display, sound, vibration, or the like. As a result of the matching processing, when authentication is valid, use in accordance with an application is enabled such as permitting use of a prescribed function of the wristband-type electronic device 1. While the registered feature value will be described as being stored in the memory unit 18 in the present embodiment, alternatively, the registered feature value may be stored in an external apparatus such as a server apparatus on the cloud or the registered feature value may be downloaded from the external apparatus when performing fingerprint authentication. In the case of the configuration described above, from the perspective of improving security, the registered feature value may be automatically deleted from the wristband-type electronic device 1 after the matching processing ends.

[Pre-Processing Unit]

Figure 7:
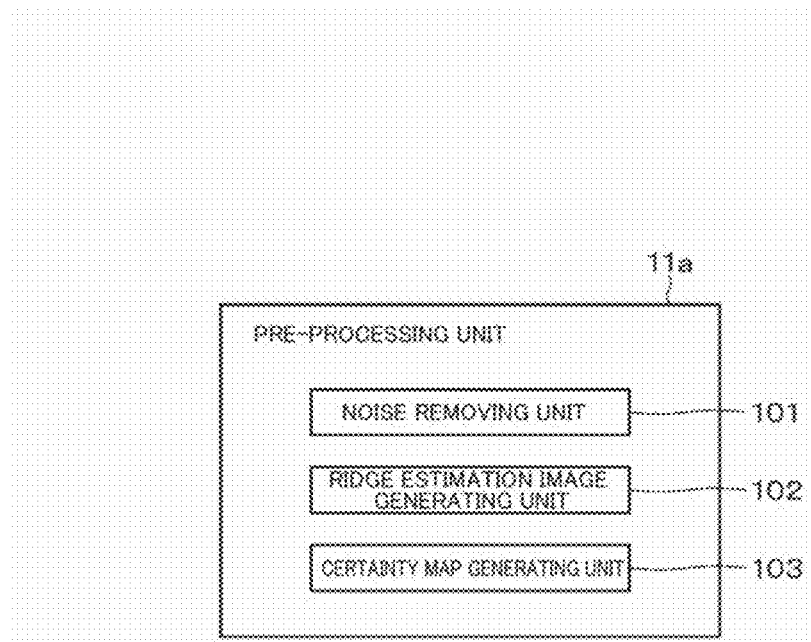
FIG. 7 is a functional block diagram for explaining an example of functions of a pre-processing unit according to the embodiment.

Next, the pre-processing unit 11a will be described. FIG. 7 is a functional block diagram for explaining an example of functions of the pre-processing unit 11a. As components that execute functions included in correction processing, for example, the pre-processing unit 11a has a noise removing unit 101, a ridge estimation image generating unit 102 as the image generating unit, and a certainty map generating unit 103.

(Noise Removing Unit)

Figure 8:
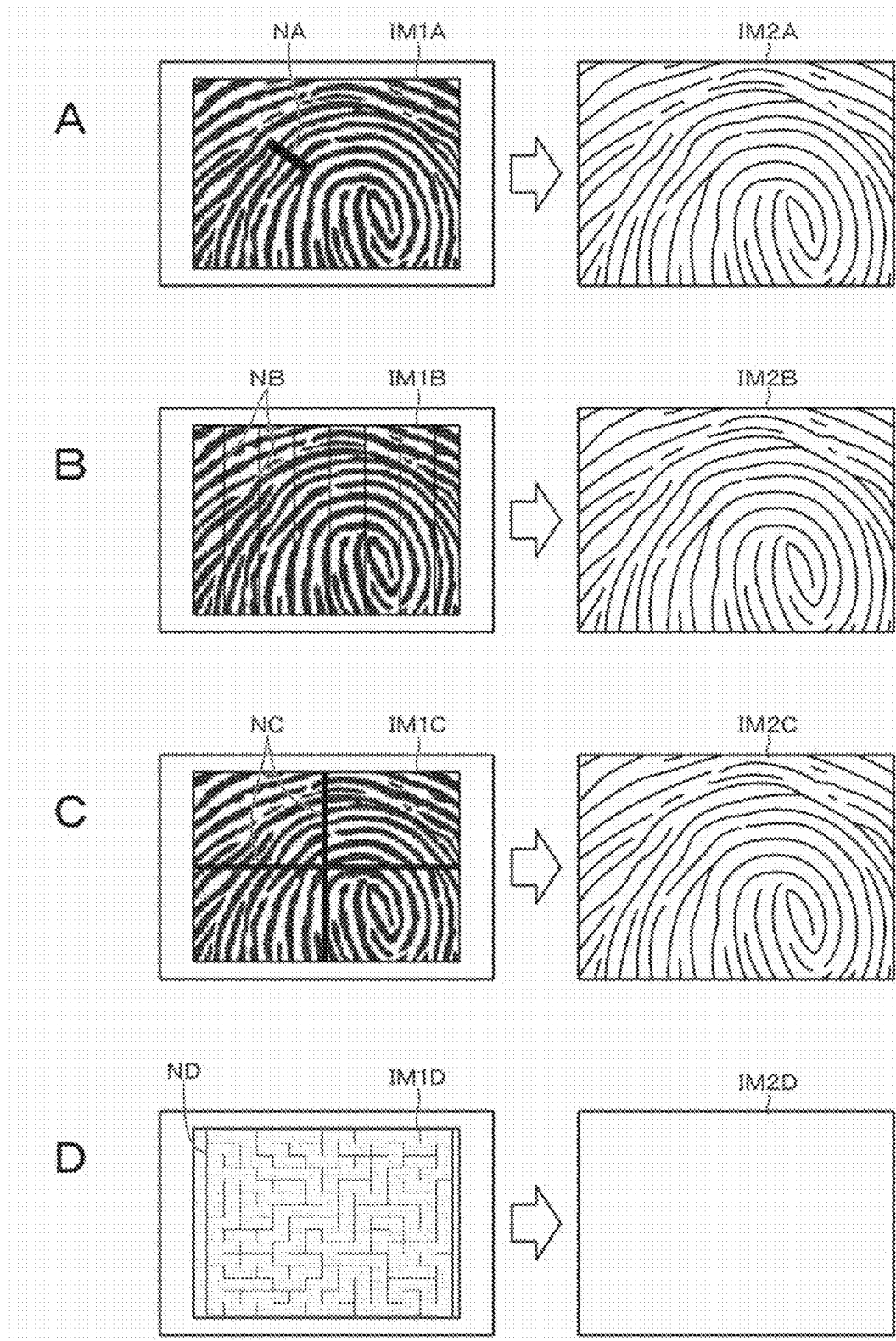
FIGS. 8A to 8D are diagrams for explaining processing by a noise removing unit according to the embodiment.

The noise removing unit 101 removes noise included in a fingerprint image. FIGS. 8A to 8D are diagrams for explaining noise removal processing that is performed by the noise removing unit 101. An image on a right side of FIG. 8A represents a fingerprint image IM1A in which a foreign particle NA appears. For example, the noise removing unit 101 determines an area in which a change in a brightness value between adjacent pixels is equal to or larger than a threshold to be a foreign particle, and removes the foreign particle NA by performing interpolation processing or the like using peripheral pixels of the foreign particle NA. Using an image obtained by removing the fingerprint image NA from the fingerprint image IM1A, a ridge estimation image IM2A such as that shown on the right side of FIG. 8A is generated by the ridge estimation image generating unit 102. Other known types of processing can be applied as the processing for removing noise such as a foreign particle. This similarly applies to processing for removing noise other than a foreign particle to be described below.

In addition, for example, the noise removing unit 101 removes a fixed pattern noise that represents noise other than a foreign particle. An image on a left side of FIG. 8B represents a fingerprint image IM1B in which, for example, a fixed pattern noise NB of a striped pattern of longitudinal lines appears. An example of the fixed pattern noise NB is a structure of the display 4 or, more specifically, a pattern included in the display 4 itself.

In the case of the structure of the wristband-type electronic device 1 according to the present embodiment, the imaging element 8 is arranged on a far side of the display 4 with an operation direction as a reference. Therefore, there is risk that a pattern included in the display 4 may appear as the fixed pattern noise NB in a fingerprint image obtained via the imaging element 8. However, since the noise removing unit 101 is configured to remove such a fixed pattern noise NB and interpolate a location of the noise NB, even in the case of the structure of the wristband-type electronic device 1 according to the present embodiment, accuracy of fingerprint authentication can be prevented from declining. Using an image obtained by removing the fixed pattern noise NB from the fingerprint image IM1B, a ridge estimation image IM2B such as that shown on the right side of FIG. 8B is generated by the ridge estimation image generating unit 102.

In addition, the noise removing unit 101 removes a boundary of an imaging element that represents noise other than a foreign particle. For example, a case where the imaging element 8 has four imaging elements as a plurality of sub-sensor units and is configured as a combination of the four imaging elements will be assumed. When specifications require that the imaging element 8 be a certain size, being able to form the imaging element 8 in the required size by combining imaging elements of an existing size is advantageous in terms of manufacturing cost and the like as compared to separately manufacturing the imaging element 8 of a new size.

However, when the imaging element 8 has a structure that combines a plurality of imaging elements, as shown on a left side of FIG. 8C, boundaries between the plurality of imaging elements appear as a noise NC in a fingerprint image IM1C. Since the noise removing unit 101 is configured to remove such a noise NC and interpolate a location of the noise NC, even in the case of the structure of the wristband-type electronic device 1 according to the present embodiment, accuracy of fingerprint authentication can be prevented from declining. Using an image obtained by removing the noise NC from the fingerprint image IM1C, a ridge estimation image IM2C such as that shown on a right side of FIG. 8C is generated by the ridge estimation image generating unit 102.

In addition, when an object that completely differs from a fingerprint appears as noise in an image obtained via the imaging element 8, the noise removing unit 101 removes the object. For example, as shown on a left side of FIG. 8D, an object that differs from a fingerprint (in the illustrated example, an object having a maze-like pattern) appears in an image IM1D as a noise ND. For example, the noise removing unit 101 determines that an object that includes no curved patterns corresponding to ridge lines is not a fingerprint and removes the pattern. An image IM2D after removal is shown on a right side of FIG. 8D. This processing is useful when, for example, clothes of the user or the like come into contact with the display 4 when performing fingerprint authentication. Alternatively, since a fingerprint does not appear in the image IM2D, processing related to fingerprint authentication may not be performed in the case of the image IM2D.

As described above, having the noise removing unit 101 perform correction processing prevents accuracy of fingerprint authentication from declining due to an effect of noise. In addition, a feedback due to a failed authentication that occurs when accuracy of fingerprint authentication declines can be prevented from being made with respect to the user.

(Ridge Estimation Image Generating Unit)

Next, the ridge estimation image generating unit 102 will be described. Based on an image subjected to processing by the noise removing unit 101, the ridge estimation image generating unit 102 generates a ridge estimation image that estimates a pattern based on a fingerprint line. Known methods of generating a ridge estimation image can be applied. Examples of a generation method of a ridge estimation image according to the present embodiment will now be described.

As a first example, the ridge estimation image generating unit 102 generates a ridge estimation image by using FFT (Fast Fourier Transform) on an image subjected to processing by the noise removing unit 101 and applying a bandpass filter around a frequency of an average cycle (for example, a 0.4 mm-cycle) of a fingerprint line of a fingerprint.

As a second example that represents another example, the ridge estimation image generating unit 102 generates a ridge estimation image by using FFT for each area that is a 1 mm by 1 mm square to extract a frequency (hereinafter, referred to as a main frequency when appropriate) that is dominant in the area and an angle of a wave (a flow direction of a fingerprint), and applying a Gabor filter that conforms to the frequency and the angle. According to the two examples described above, a main ridge line/valley line is enhanced and an effect of a small noise can be reduced.

Figure 9:
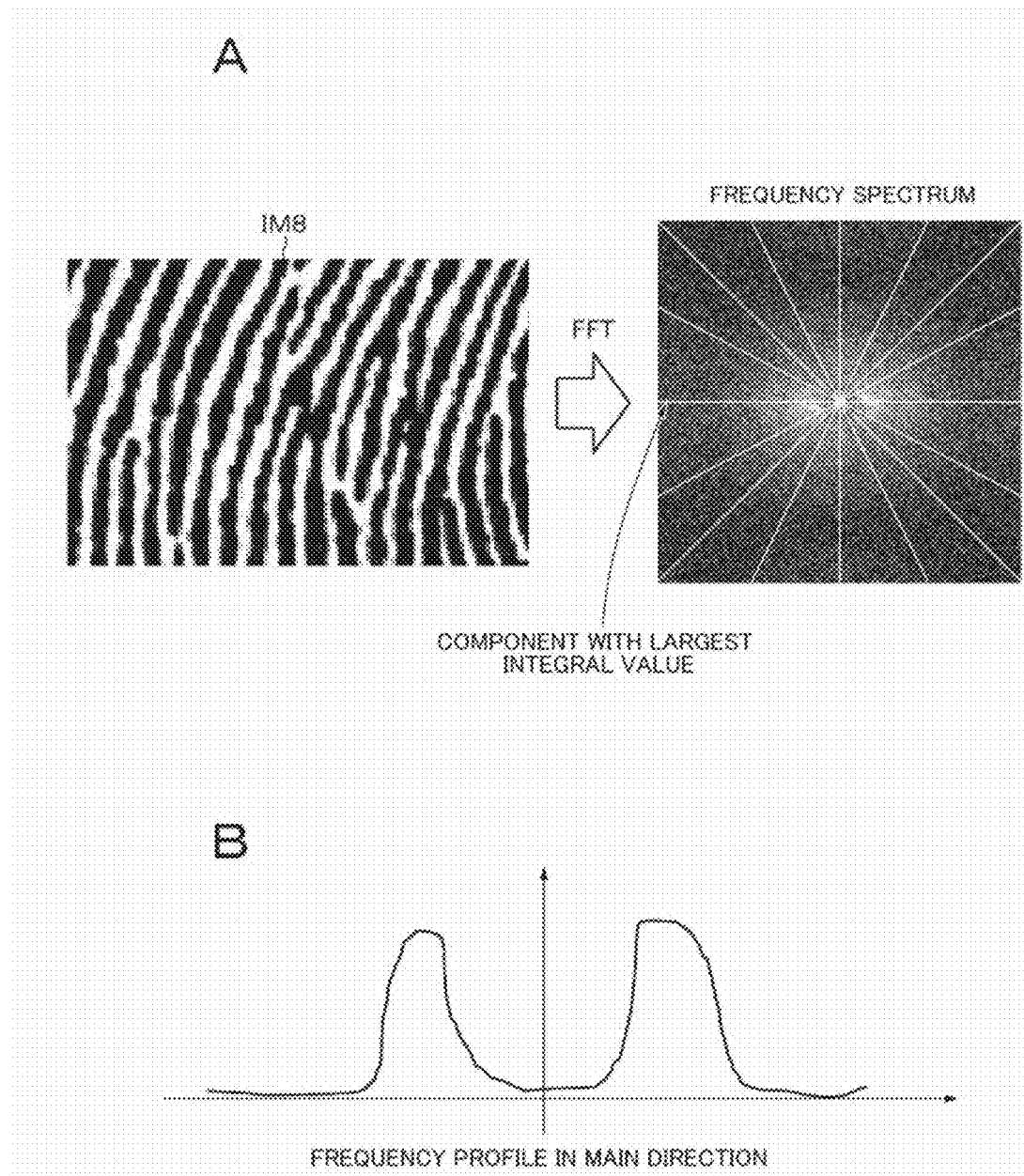
FIGS. 9A and 9B are diagrams to be referred to when explaining an example of processing for detecting a direction of a flow of a fingerprint and a main frequency.

In the second example, an example of a method of detecting a flow direction of a fingerprint and a main frequency will be described with reference to FIG. 9. An image IM8 shown on a left side of FIG. 9A represents a given fingerprint image IM8. In addition, a frequency spectrum obtained by applying FFT to the image IM8 is shown on a right side of FIG. 9A. One line among radial lines superimposed on the frequency spectrum indicates a component with a largest integral value to be described later. In addition, FIG. 9B shows a frequency profile in a direction (a main direction) of the component with the largest integral value.

As a first step, profiles are extracted with respect to 16 directions of the frequency spectrum and a direction with a largest integral value is determined. This is considered a directional component of a main wave. As a subsequent second step, a peak value is detected from the frequency profile in the main direction and a frequency corresponding to the peak value is adopted as a main frequency. In this manner, a flow direction of a fingerprint and a main frequency can be detected.

Figure 10:
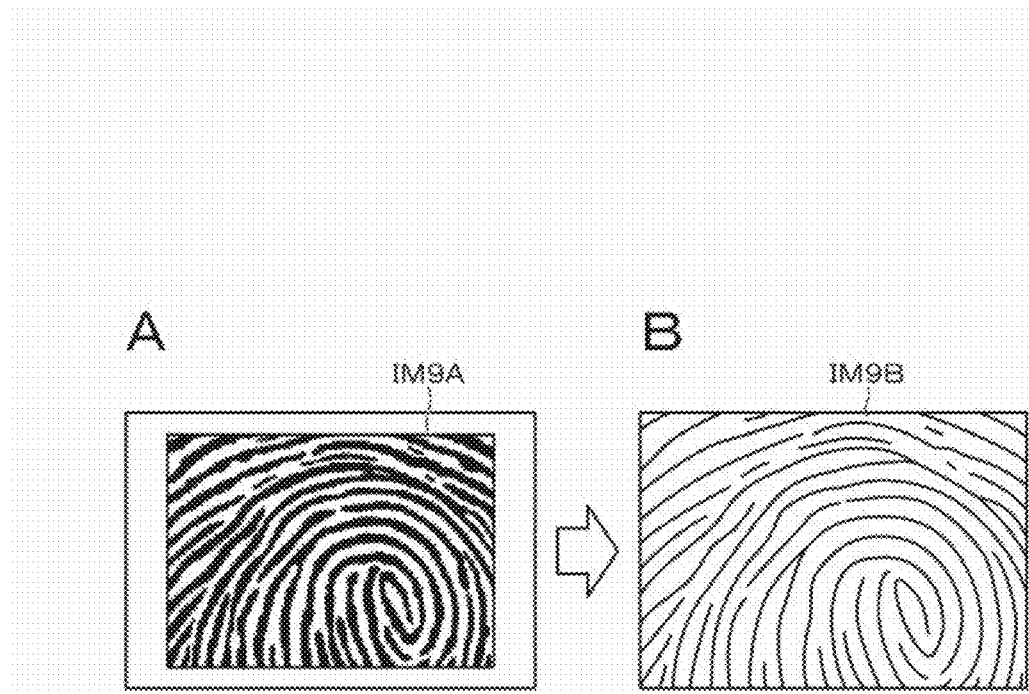
FIGS. 10A and 10B are diagrams for explaining processing for estimating a fingerprint line to the outside of a photographing range.

The ridge estimation image generating unit 102 according to the present embodiment is configured to estimate a pattern of a fingerprint over an expanded area of a photographed area that exceeds the photographed area by a prescribed range. For example, based on a fingerprint image IM9A shown in FIG. 10A, a ridge estimation image IM9B having been enlarged to a range that is larger by a prescribed size than the fingerprint image IM9A is generated as shown in FIG. 10B. For example, a fingerprint line obtained in an original size (a size of the fingerprint image IM9A) is extended along a flow (an orientation) of the fingerprint line. According to the processing, there may be cases in which a position where a prescribed fingerprint line and a fingerprint line that differs therefrom unite or, in other words, a bifurcation or an intersection of the fingerprint line which is one of the feature points of the fingerprint described earlier can be obtained. According to the processing described above, for example, even when the size of the imaging element 8 is small and there is a limit to an area of an image that is obtained by the imaging element 8, a larger number of feature points can obtained and accuracy of fingerprint authentication can be improved.

(Certainty Map Generating Unit)

Next, the certainty map generating unit 103 will be described. The certainty map generating unit 103 generates a certainty map that indicates a certainty of a result of an estimation among an area of a ridge estimation image that is an image representing an estimation of a pattern corresponding to a fingerprint.

Figure 11:
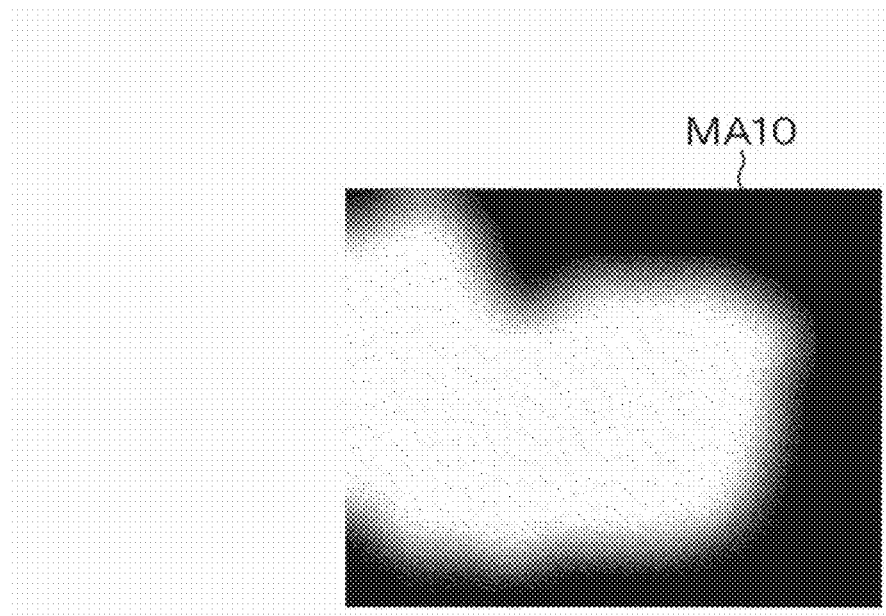
FIG. 11 is a diagram showing an example of a certainty map.

FIG. 11 shows a certainty map MA10 that represents an example of a certainty map. In the certainty map MA10 shown in FIG. 11, an area of an image is divided into a white area and a black area. In the present example, the white area is considered an area with high certainty or, in other words, an area in which a pattern of a fingerprint line is conceivably accurately obtained. On the other hand, the black area is an area with low certainty. A prescribed threshold with respect to certainty is set, an area with high certainty is set when the certainty is equal to or higher than the threshold, and an area with low certainty is set when the certainty is lower than the threshold.

An example related to certainty will now be described. For example, an image with a prescribed size (for example, a 1 mm×1 mm rectangular image) is cut out from an image. In addition, with respect to the cut out image, a brightness distribution indicating a distribution of brightness values included in each pixel is created.

Figure 12:
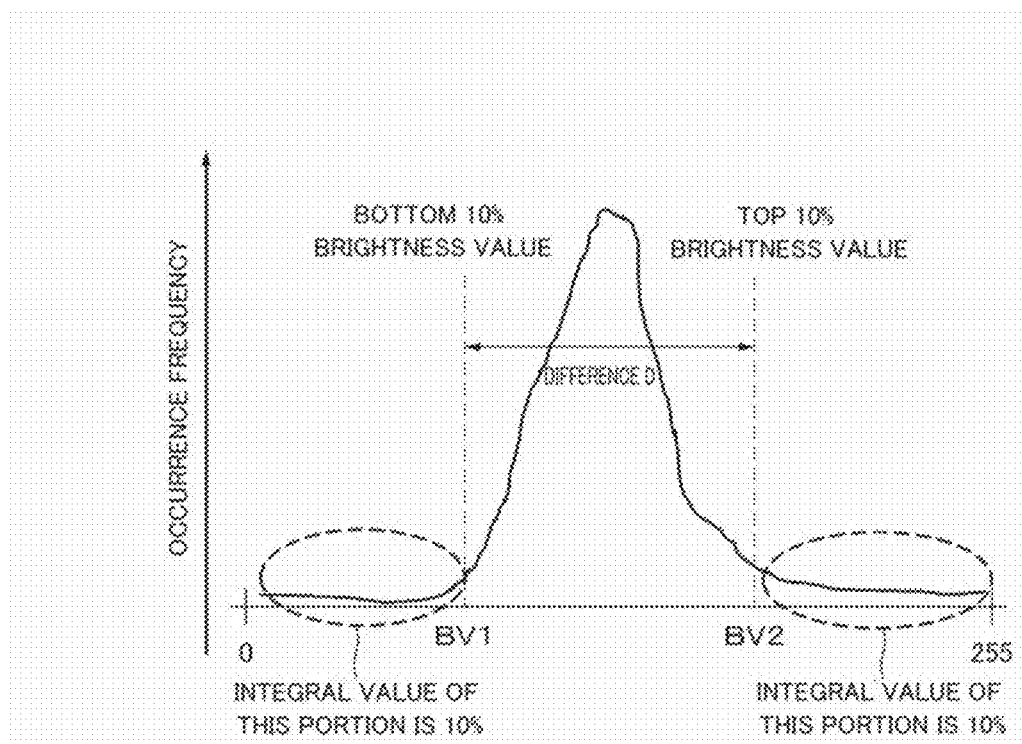
FIG. 12 is a diagram for explaining an example of certainty.

FIG. 12 shows an example of a brightness distribution. Let a brightness value at which an integral value obtained by integrating upward a frequency distribution $Pi$ ($i=0, \ldots, 255$) of brightness reaches 10% or, in other words, a 10-percentile brightness value where $$\Sigma_0^{BV1} Pi = 0.1$$

be denoted by BV1, and a brightness value at which an integral value obtained by integrating downward the frequency distribution $Pi$ of brightness reaches 10% or, in other words, a 90-percentile brightness value where $$\Sigma_{BV2}^{255} Pi = 0.1$$

be denoted by BV2. A difference value D between the brightness value BV1 and the brightness value BV2 is set as certainty. Alternatively, a dispersion of brightness values of the cut out image may be adopted as certainty.

The function of the ridge estimation image generating unit 102 and the function of the certainty map generating unit 103 described above may be constructed as a single function block and the function block may be configured to generate a certainty-added ridge estimation image.

Figure 13:
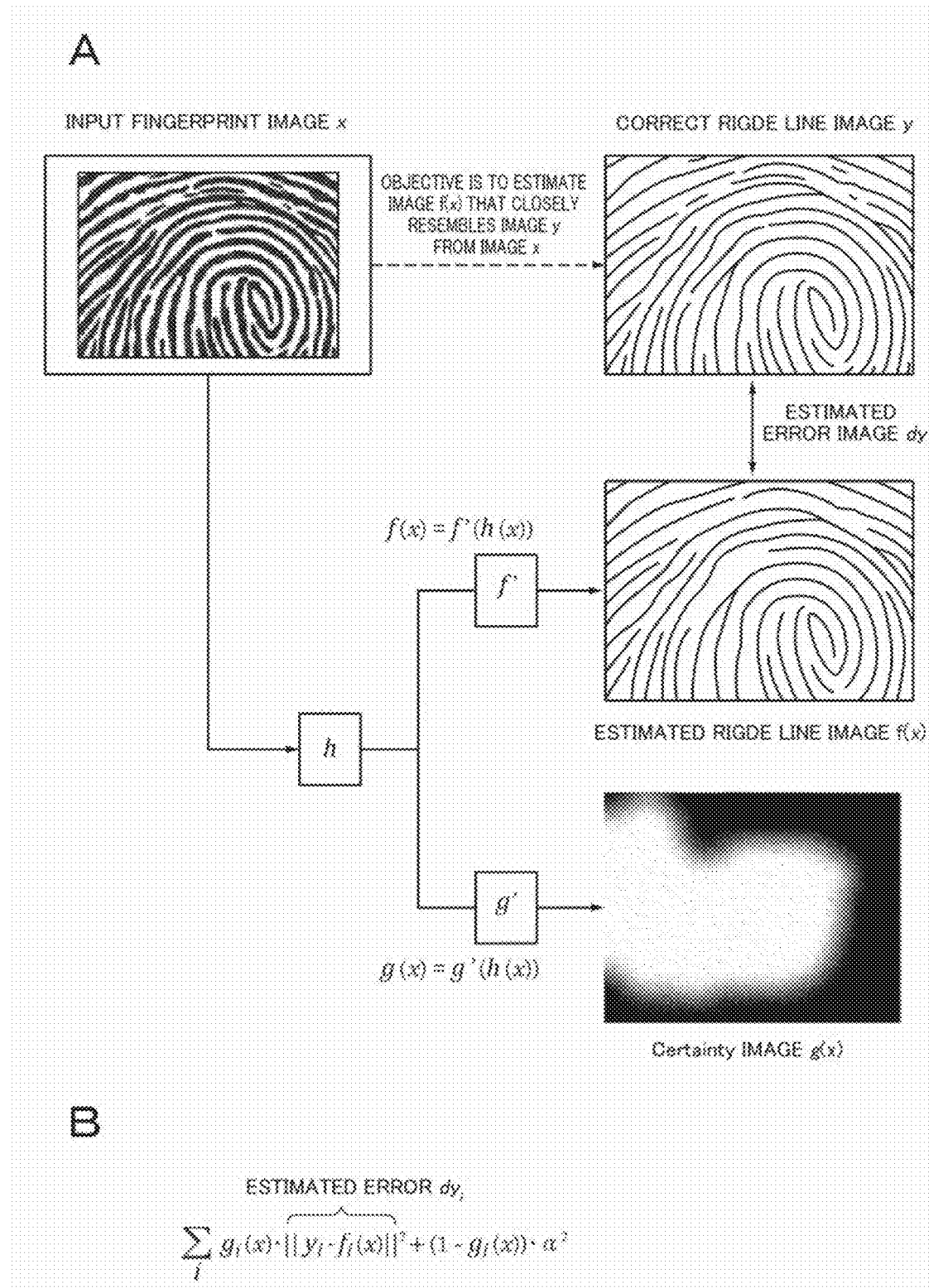
FIGS. 13A and 13B are diagrams for explaining processing for generating a ridge estimation image with a certainty map.

An example of a generation method of a certainty-added ridge estimation image will be described with reference to FIG. 13. As shown in FIG. 13A, an operation by a function h and a function f' is performed with respect to an input fingerprint image x to obtain a ridge estimation image f(x) (where f(x)=f'(h(x))).

In addition, an operation by the function h and a function g' is performed with respect to the input fingerprint image x to obtain a Certainty image g(x) (where g(x)=g'(h(x))) which is a certainty map. In the Certainty image g(x), a white area is an area that can likely be recognized with an error of a or less and a black area is an area that cannot be kept to or below the error a.

A ridge line image that is correct with respect to the input fingerprint image x will be referred to as a correct ridge line image y. An estimated error between the correct ridge line image y and the ridge estimation image f(x) will be referred to as an estimated error dy.

An object of processing is to estimate an image f(x) that closely resembles y from x. In addition, another object is to recognize an area that can likely be correctly estimated or, in other words, to determine whether not the estimated error can likely be kept to or below a in an area.

The control unit 11 simultaneously learns functions f and g (where $0 \leq g(x) \leq 1$) which minimizes a loss function shown in FIG. 13B. A portion bracketed in the loss function shown in FIG. 13B represents an estimated error dyi.

In this case, since "gi(x)·dyi+(1−gi(x))·α" is minimized, a force that increases Certainty gi(x) acts with respect to a pixel where an error of valley line estimation is likely to be dyi<α.

On the other hand, with respect to a pixel where an error of valley line estimation is likely to be dyi>α, a force that reduces Certainty gi(x) acts. As a result, by minimizing "gi(x)·dyi+(1−gi(x))·a", Certainty gi(x) is optimized so as to indicate a magnitude at which an error of valley line estimation is likely to be dyi<α.

[Flow of Processing]

(Registration Processing)

Figure 14:
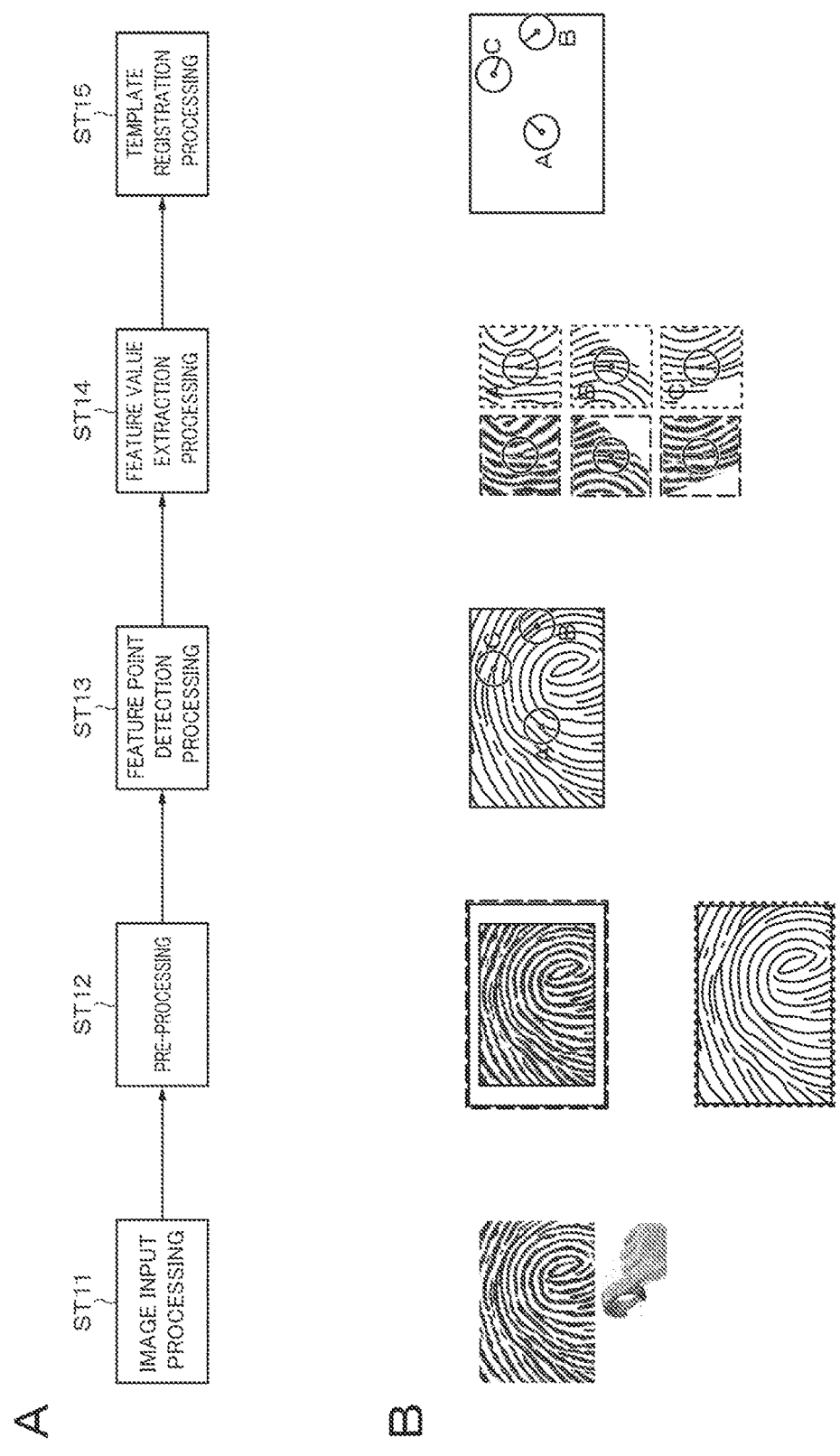
FIGS. 14A and 14B are diagrams for explaining registration processing according to the embodiment.

Next, a flow of processing performed by the wristband-type electronic device 1 will be described. First, registration processing for registering a feature value that corresponds to a feature point of a fingerprint will be described with reference to FIG. 14. FIG. 14A is a diagram showing a flow of the registration processing. In addition, FIG. 14B is a diagram showing, in association with each step of processing, an image or the like obtained in each step of processing.

In step ST11, image input processing is performed. For example, a fingertip comes into contact with the display 4 and a fingerprint image is acquired via the imaging element 8. The light-emitting unit 6 emits light when fingerprint authentication is acquired. Subsequently, the processing advances to step ST12.

In step ST12, pre-processing by the pre-processing unit 11a is performed. Specifically, noise is removed from the fingerprint image by the noise removing unit 101. In addition, based on the fingerprint image from which noise has been removed, the ridge estimation image generating unit 102 generates a ridge estimation image. Furthermore, the certainty map generating unit 103 generates a certainty map. In FIG. 14B, illustration of the certainty map has been omitted. Subsequently, the processing advances to step ST13.

In step ST13, the feature point detecting unit 11b detects a feature point of a fingerprint based on the ridge estimation image. In the present embodiment, the feature point detecting unit 11b refers to the certainty map and detects a feature point from inside an area determined to have certainty of a certain level or higher. FIG. 14B shows an example in which three feature points (centers of circled locations) are detected. Subsequently, the processing advances to step ST14.

In step ST14, the feature value extracting unit 11e extracts a feature value that characterizes each feature point. As described above, the feature value extracting unit 11c cuts out an image having a prescribed size and being centered on each feature point and extracts a feature value based on the cut out image. Subsequently, the processing advances to step ST15.

In step ST15, the control unit 11 performs template registration processing for registering a feature value of each feature point extracted by the processing in step ST14. A feature value of each feature point is stored in, for example, the memory unit 28. The feature value stored in the memory unit 28 is used as a registered feature value in matching processing to be described later.

(Matching Processing)

Figure 15:
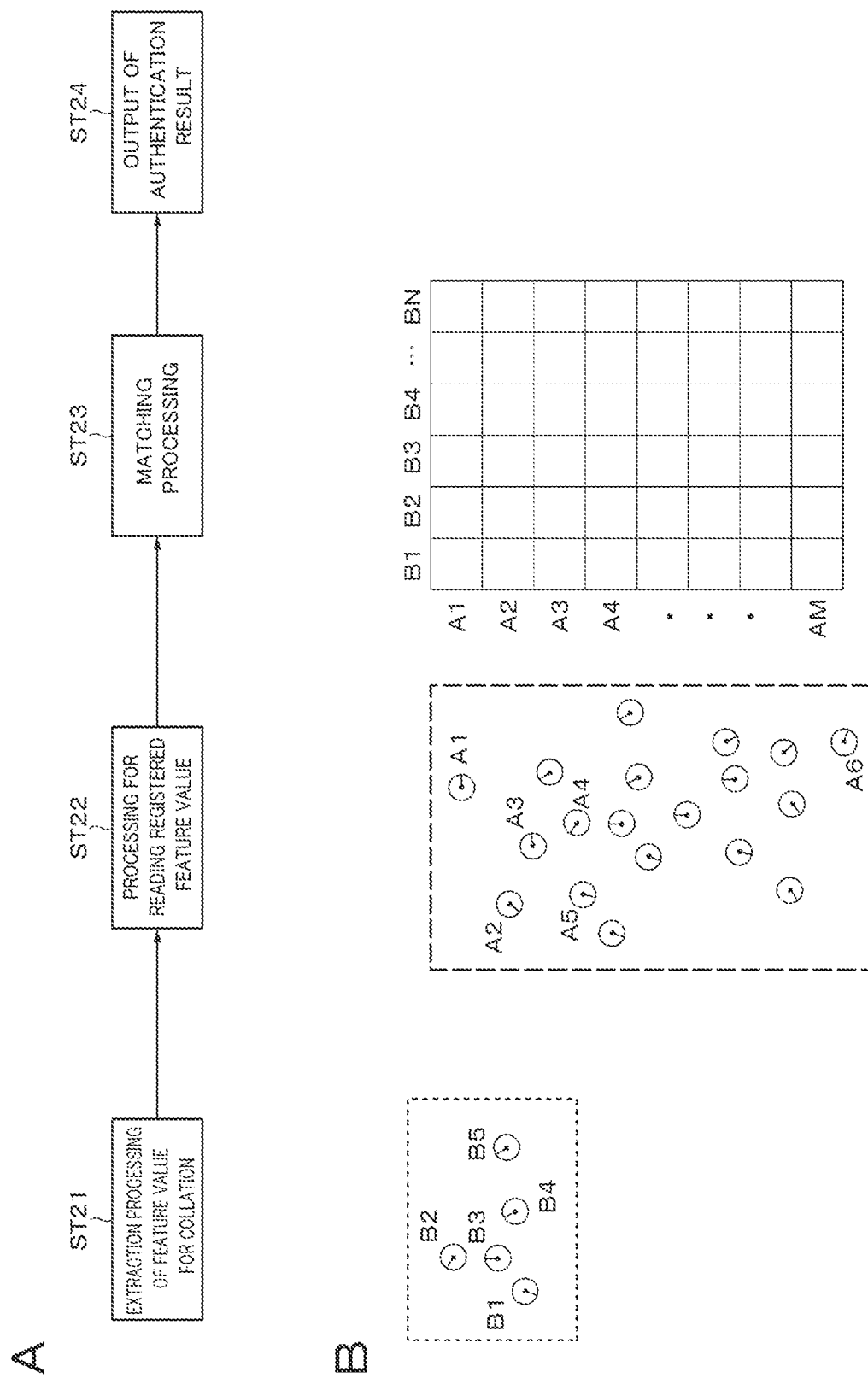
FIGS. 15A and 15B are diagrams for explaining matching processing according to the embodiment.

Next, matching processing will be described with reference to FIG. 15. FIG. 15A is a diagram showing a flow of the matching processing. FIG. 15B is a diagram showing an example of a feature value acquired in each step of processing and diagrams that are referred to when describing processing contents being associated with the respective steps of processing.

In step ST21, a fingertip is placed on the display 4 and a fingerprint image is acquired. In addition, feature value extraction processing for extracting a feature value is performed. The feature value extraction processing in step ST21 is processing including steps ST11 to ST14 described above. A feature value for collation for performing fingerprint authentication is acquired through the processing of step ST21. FIG. 15B shows feature values corresponding to five feature points. Subsequently, the processing advances to step ST22.

In ST22, the control unit 11 reads registered feature values from the memory unit 28. FIG. 15B shows an example of registered feature values. Subsequently, the processing advances to step ST23.

In step ST23, the matching processing unit 11d performs matching processing for collating a feature value acquired in the processing of step ST21 with a registered feature value read in step ST22.

An example of the matching processing will be described. The matching processing unit 11d obtains a similarity score between the feature value for collation and the registered feature value by inner product calculation and, based on a result thereof, generates a similarity score matrix shown in FIG. 15B. In the similarity score matrix, "A" represents a feature point that is already registered and "B" represents a feature point for collation. An (i, j) component represents a similarity score between Ai and Bi.

Based on the similarity score matrix, the matching processing unit 11d calculates a collated score. When the collated score is equal to or higher than a threshold, fingerprint authentication is valid. When the collated score is lower than the threshold, the fingerprint authentication is invalid. For example, a maximum value in the similarity score matrix is set as the collated score. An average value in the similarity score matrix may be set as the collated score. An average value of maximum values of the respective columns in the similarity score matrix may be set as the collated score.

According to the first embodiment described above, since a feature value is to be extracted based on a peripheral image of a feature point, information other than information on the feature point itself can be adopted as a feature value of the feature point. Since performing matching processing using such a feature value enables matching processing based on various types of information to be performed, accuracy of fingerprint authentication can be improved.

Second Embodiment

Next, a second embodiment will be described. It should be noted that matters (for example, a configuration and functions of the wristband-type electronic device 1) described in the first embodiment can also be applied to the second embodiment unless specifically stated to the contrary.

As also described in the first embodiment, the wristband-type electronic device 1 is configured to perform fingerprint authentication using the imaging element 8. Generally, sensing using an imaging element (as a more specific example, a CMOS sensor) has a problem in that power consumption is greater than sensing according to other systems (for example, an electrostatic capacitance system). While a battery with a capacity in accordance with required power may be used, wearable devices are constrained in terms of a size of a battery that can be mounted and there is a limit to the capacity of batteries. Therefore, unnecessary consumption of power is desirably suppressed as much as possible.

In addition, wearable devices are also constrained in terms of the number and sizes of input devices such as buttons to be arranged thereon. Therefore, control for suppressing unnecessary consumption of power as much as possible is desirably executed without being triggered by an operation with respect to a physical device such as a button. In consideration of these perspectives, the second embodiment will now be described in detail.

[State Transition]

Figure 16:
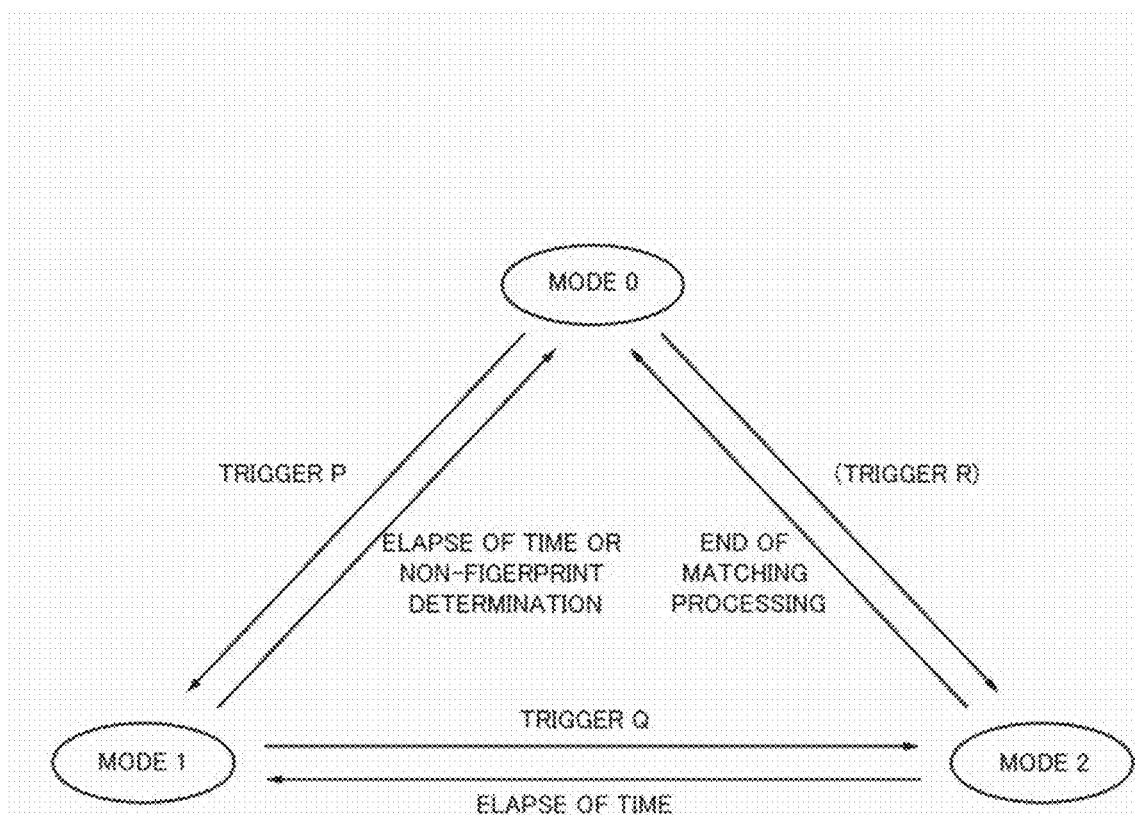
FIG. 16 is a state transition diagram for explaining an example of transitions of operating modes.

FIG. 16 is a diagram showing state transitions of the wristband-type electronic device 1. As operating modes related to fingerprint authentication, the wristband-type electronic device 1 is configured so as to be capable of making transitions among, for example, three modes. The three modes are mode 0, mode 1, and mode 2. From the perspective of power consumption, mode 0 minimizes power consumption and mode 2 maximizes power consumption. The power consumption in mode 1 is larger than the power consumption in mode 0 but smaller than the power consumption in mode 2. Mode 0 corresponds to an example of the third mode and modes 1 and 2 respectively correspond to examples of the first and second modes.

[Operations in Each Mode]

Next, an example of operations in each mode will be described. In each mode, all of contents of operations described below need not be performed and at least one operation may be performed.

(Outline of Operation Contents)

Mode 0 is a quiescent state and a mode in which the light-emitting unit 6 is turned off and the imaging element 8 is not operated or, in other words, sensing of a fingerprint using the imaging element 8 is not performed.

Mode 1 is a standby state and a mode in which the light-emitting unit 6 is turned on and sensing of a fingerprint using the imaging element 8 is performed.

Sensing in mode 1 may be sensing in such a degree that a determination can be made as to whether or not an object in contact with the display 4 is a fingerprint.

More specifically, the sensing may acquire an image in a degree that enables a determination to be made as to whether or not a fingerprint (for example, a feature point of a fingerprint) is included.

Mode 2 is an authenticating state and a mode in which the light-emitting unit 6 is turned on, a feature value of a fingerprint is acquired, and matching processing for collating the acquired feature value with a registered feature value is performed. In addition, in mode 2, an image is acquired via the imaging element 8 based on a setting that differs from a setting of mode 1.

For example, when a feature point of a fingerprint is detected from an image and an object in contact with the display 4 is determined to be a fingertip in mode 1, the operating mode makes a transition to mode 2 in which power consumption increases. Due to the mode transition, even when an object other than a fingertip such as clothes comes into contact with the display 4, matching processing and the like which consume a large amount of power are prevented from being unnecessarily performed. Therefore, for example, a drop in capacity of a battery can be suppressed.

(Specific Example of Operations in Each Mode)

A specific example of operations in each mode will be described. Mode 0 is a mode in which processing related to fingerprint authentication is not performed. Therefore, specific examples of operations in mode 1 and mode 2 will be described below.

As a first example, for instance, the control unit 11 performs lighting control for controlling luminance of the light-emitting unit 6. In accordance with the lighting control, operations in each mode are performed. For example, in mode 1, since a feature point of a fingerprint need only be obtained, luminance (brightness) of the light-emitting unit 6 is set low. On the other hand, in mode 2, since matching processing must be performed, a feature value such as a position of a sweat gland must be acquired from a peripheral image of the feature point. Therefore, the luminance of the light-emitting unit 6 is increased from mode 1 so that a high-definition image may be obtained. Since intensity of reflected light from a fingertip varies depending on a state of the finger or a degree of pressing by the finger, light-emitting intensity of the light-emitting unit 6 may further be adaptively adjusted based on brightness of an image.

As a second example, for instance, the control unit 11 performs resolution control for changing resolution by controlling a pixel to become active in the imaging element 8. In accordance with the resolution control, operations in each mode are performed. For example, in mode 1, low resolution is set and sensing is performed in low resolution. Low resolution refers to, for example, a resolution of around 300 to 500 ppi (pixel per inch) at which a feature point of a fingerprint can be detected. In mode 2, high resolution is set and sensing is performed in high resolution. High resolution refers to, for example, a resolution of around 1000 ppi or higher at which features that are even finer than a fingerprint line such as a sweat gland can be photographed.

As a third example, for instance, the control unit 11 performs sensing area control for controlling a sensing area that is an imaging range by controlling an area of pixels to become active in the imaging element 8. In mode 1, sensing using a portion (for example, only near a center) of the imaging element 8 is performed. In mode 2, sensing using the entire imaging element 8 is performed.

Control that combines the controls in the examples described above may be performed. For example, in mode 1, sensing in low resolution is performed using the entire imaging element 8 to detect a feature point of a fingerprint. In mode 2, only an area near the detected feature point may be subjected to sensing in high resolution.

[State Transitions Between Modes]

Next, transitions between modes will be described. Transitions between operating modes occur in accordance with a prescribed trigger, elapse of time, a result of processing, or the like. As shown in FIG. 16, a transition from mode 0 to mode 1 occurs based on a trigger P. In addition, a transition from mode 1 to mode 2 occurs based on a trigger Q.

In processing when the operating mode is mode 1 or, more specifically, in determination processing based on an image, when the object having come into contact with the display 4 is not a fingerprint, the operating mode makes a transition from mode 1 to mode 0. In addition, when a state where the operating mode is mode 1 continues for a prescribed period of time, the operating mode makes a transition from mode 1 to mode 0 (timeout).

When a state where the operating mode is mode 2 continues for a prescribed period of time, the operating mode makes a transition from mode 2 to mode 1 (timeout). In addition, in a case where matching processing ends when the operating mode is mode 2 and a result of fingerprint authentication is obtained, the operating mode makes a transition from mode 2 to mode 0.

Alternatively, the operating mode may be enabled to make a transition directly from mode 0 to mode 2. For example, the operating mode may be enabled to make a transition from mode 0 to mode 2 based on a trigger R. An example of the trigger R is an input of an operation for instructing fingerprint authentication to be performed. In this case, since it is apparent in advance that fingerprint authentication is to be performed, the operating mode may be enabled to make a transition directly from mode 0 to mode 2.

[Specific Examples of Triggers]

Next, specific examples of triggers will be described. Since a specific example of the trigger R has already been described, a redundant description will be omitted.

(Specific Example of Trigger P)

An example of the trigger P is a timing at which start of use of the wristband-type electronic device 1 is detected. At a timing at which the start of use of the wristband-type electronic device 1 is detected, it is assumed that the likelihood of fingerprint authentication being performed in order to execute a prescribed application is high. Therefore, the operating mode makes a transition from mode 0 to mode 1.

Figure 17:
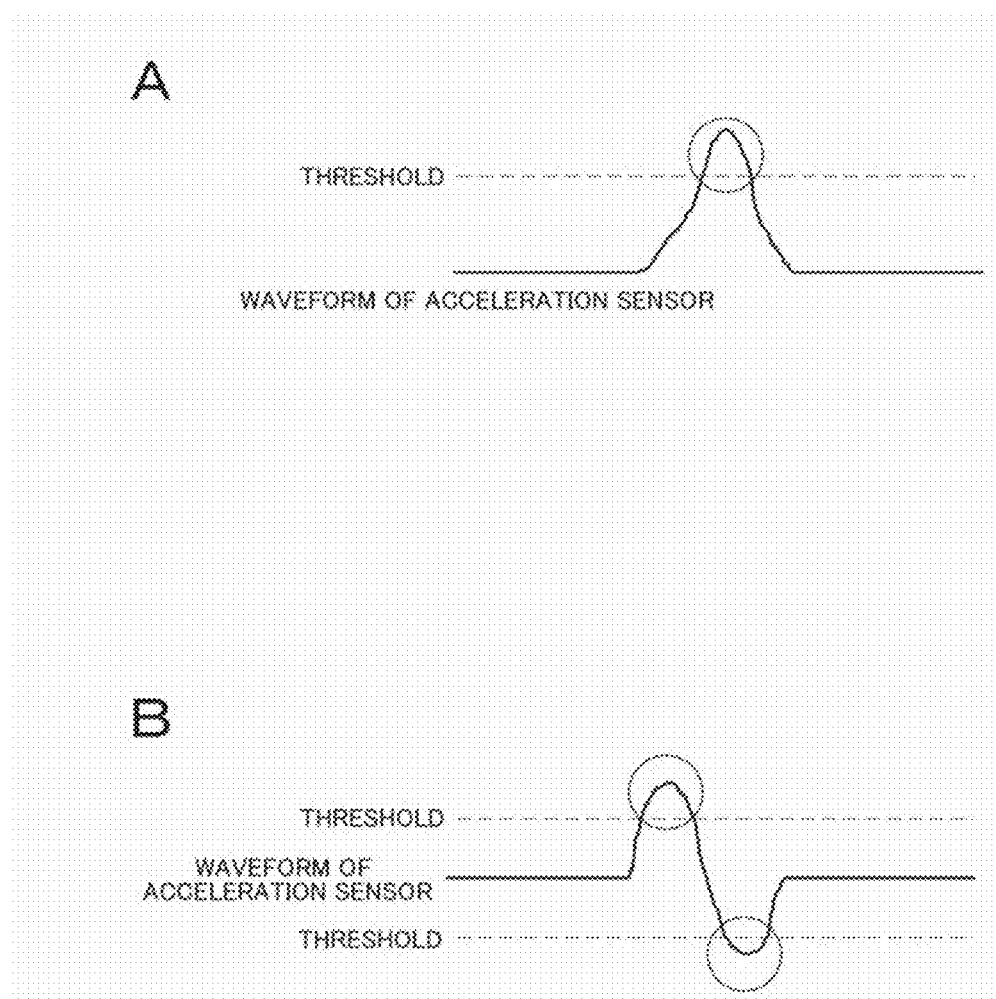
FIGS. 17A and 17B are diagrams for explaining an example of a trigger P.

A more specific example of the trigger P is, as shown in FIGS. 17A and 17B, a waveform of an acceleration sensor (an output of an acceleration sensor) or a change in output of the acceleration sensor becoming equal to or greater than a threshold or equal to or smaller than the threshold. In this case, since the likelihood of the wristband-type electronic device 1 being used is high, the operating mode makes a transition from mode 0 to mode 1. An acceleration sensor can be applied as one of the motion sensors 20.

Figure 18:
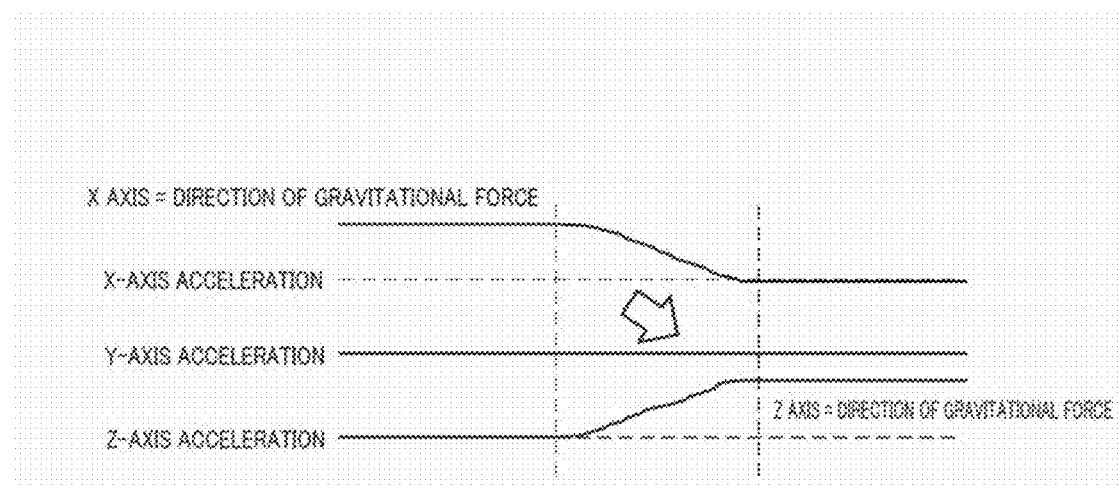
FIG. 18 is a diagram for explaining another example of the trigger P.
Figure 19:
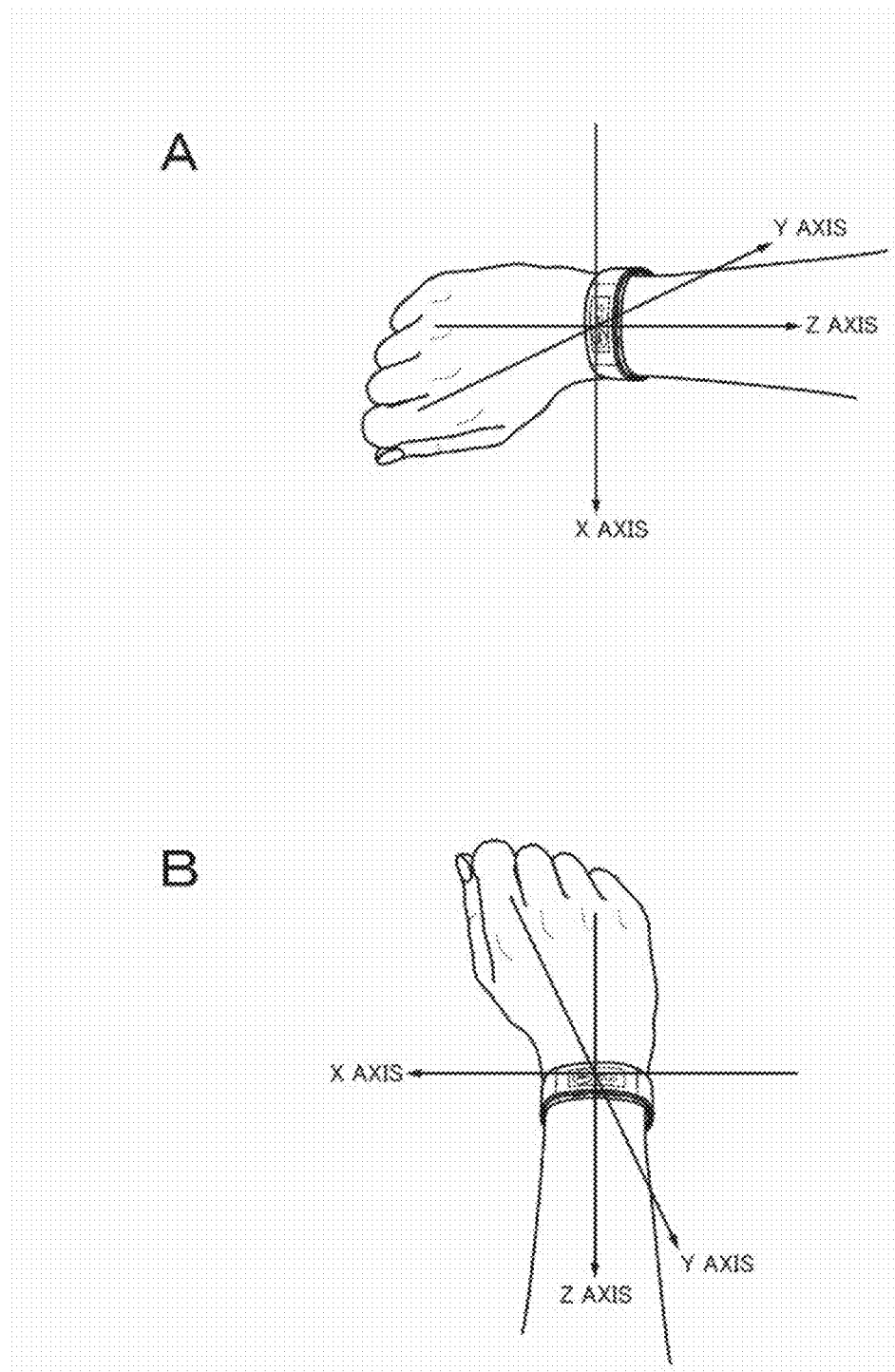
FIGS. 19A and 19B are diagrams for explaining an example of axial directions that are defined by a wristband-type electronic device.

Another specific example of the trigger P is, as shown in FIG. 18, an occurrence of a change equal to or greater than a threshold in a direction of a resultant vector of triaxial acceleration (a direction of gravitational force). For example, a sensor output corresponding to each axis is defined in the motion sensor 20 of the wristband-type electronic device 1. Examples of the respective axes that correspond to the wristband-type electronic device 1 are shown in FIGS. 19A and 19B. When triaxial acceleration is represented by a three-dimensional vector and a direction of the three-dimensional vector changes, a determination is made that an orientation of a hand has changed. Even in this case, since the likelihood of some sort of action including fingerprint authentication to be performed with respect to the wristband-type electronic device 1 is high, the operating mode makes a transition from mode 0 to mode 1.

Figure 20:
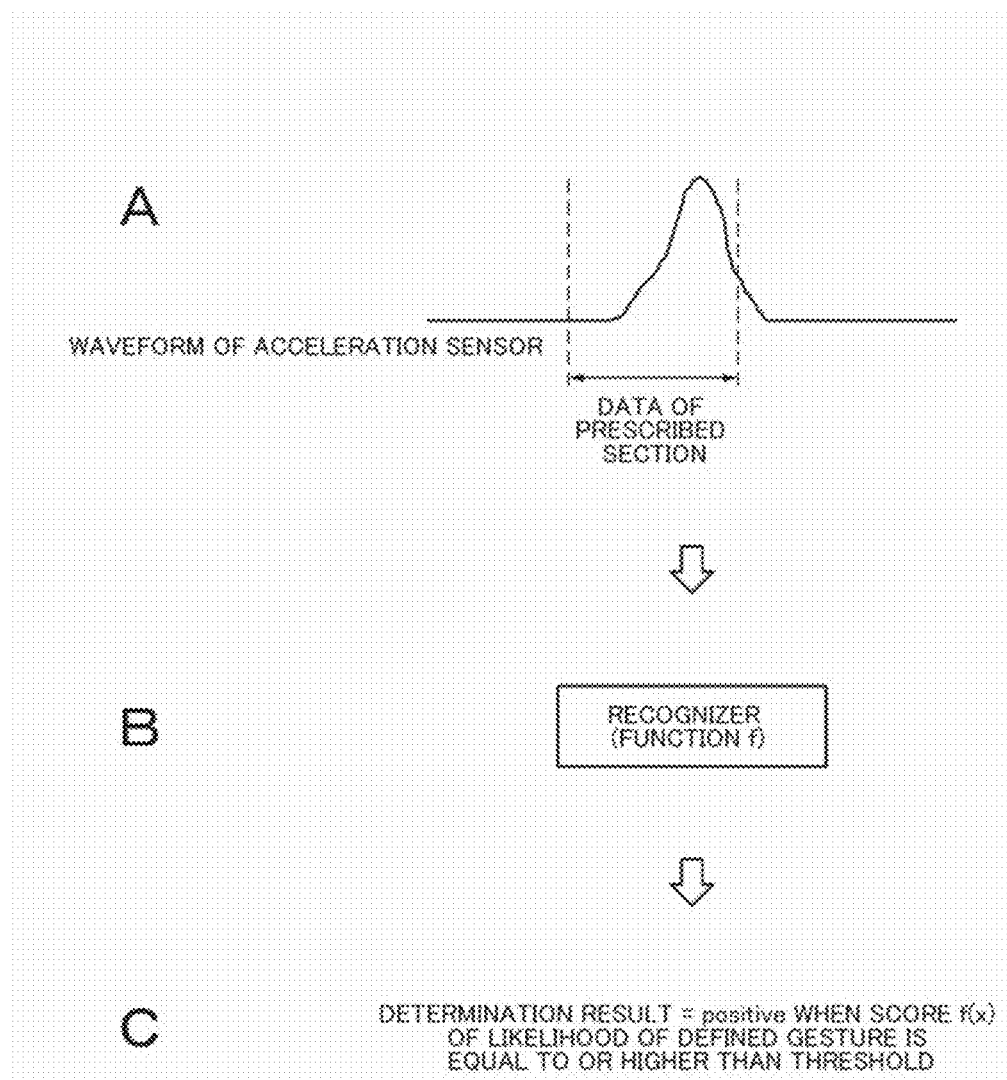
FIGS. 20A to 20C are diagrams for explaining another example of the trigger P.

Another specific example of the trigger P will be described with reference to FIG. 20. As shown in FIG. 20A, a prescribed section is set so as to include a location where a change equal to or greater than a threshold has occurred in the output of the acceleration sensor. The output of the acceleration sensor which corresponds to the set prescribed section is input to a recognizer that is schematically shown in FIG. 20B. The recognizer is configured to determine whether or not a prescribed gesture has been made by applying a function f to the output of the acceleration sensor.

As a result of processing by the recognizer, a determination result of the recognizer is obtained as shown in FIG. 20C. A case where a score f(x) which indicates a likelihood of a defined gesture and which represents the determination result is equal to or higher than a threshold is adopted as the trigger P. When a gesture in a state where the wristband-type electronic device 1 is worn is detected, the likelihood of some sort of action including fingerprint authentication to be performed with respect to the wristband-type electronic device 1 is high. Therefore, the operating mode makes a transition from mode 0 to mode 1.

Figure 21:
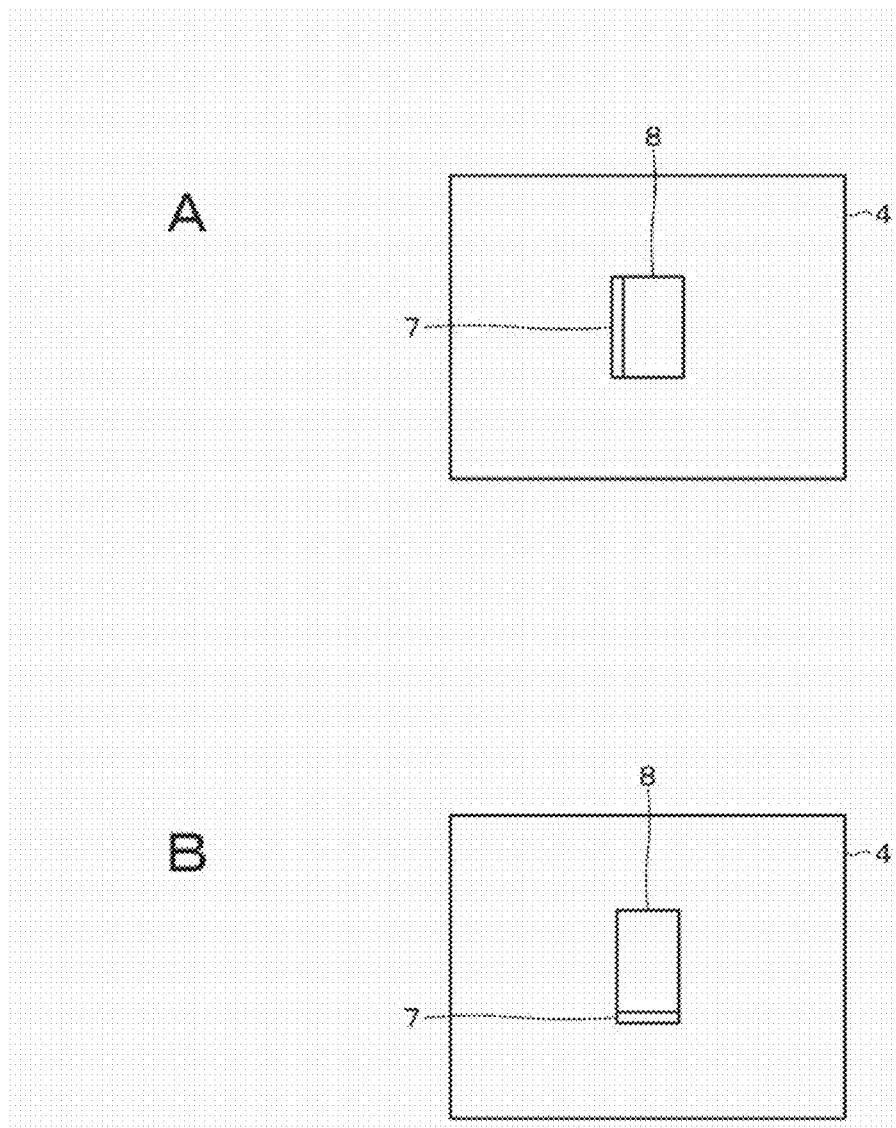
FIGS. 21A and 21B are diagrams to be referred to when explaining another example of the trigger P.

The trigger P may be a case where a contact of a fingertip with the display 4 or a movement of the fingertip in contact with the display 4 is detected. A case where a contact by an object of some kind instead of a fingertip or a movement of the object is detected may be set as the trigger P. FIGS. 21A and 21B are diagrams schematically showing respective positions of the imaging element 8 and the touch sensor unit 7 with respect to the display 4. For example, as shown in FIGS. 21A and 21B, the touch sensor unit 7 that detects a contact or a movement by an object is arranged in a vicinity of the imaging element 8.

While specific examples of the trigger P have been described above, the trigger P is not limited thereto and various conditions can be set as the trigger P. A condition created by combining the examples described above may be adopted as the trigger P.

(Specific Example of Trigger Q)

Next, a specific example of the trigger Q will be described. The trigger Q is, for example, a trigger contingent on a fingerprint being included in an image obtained via the imaging element 8.

Figure 22:
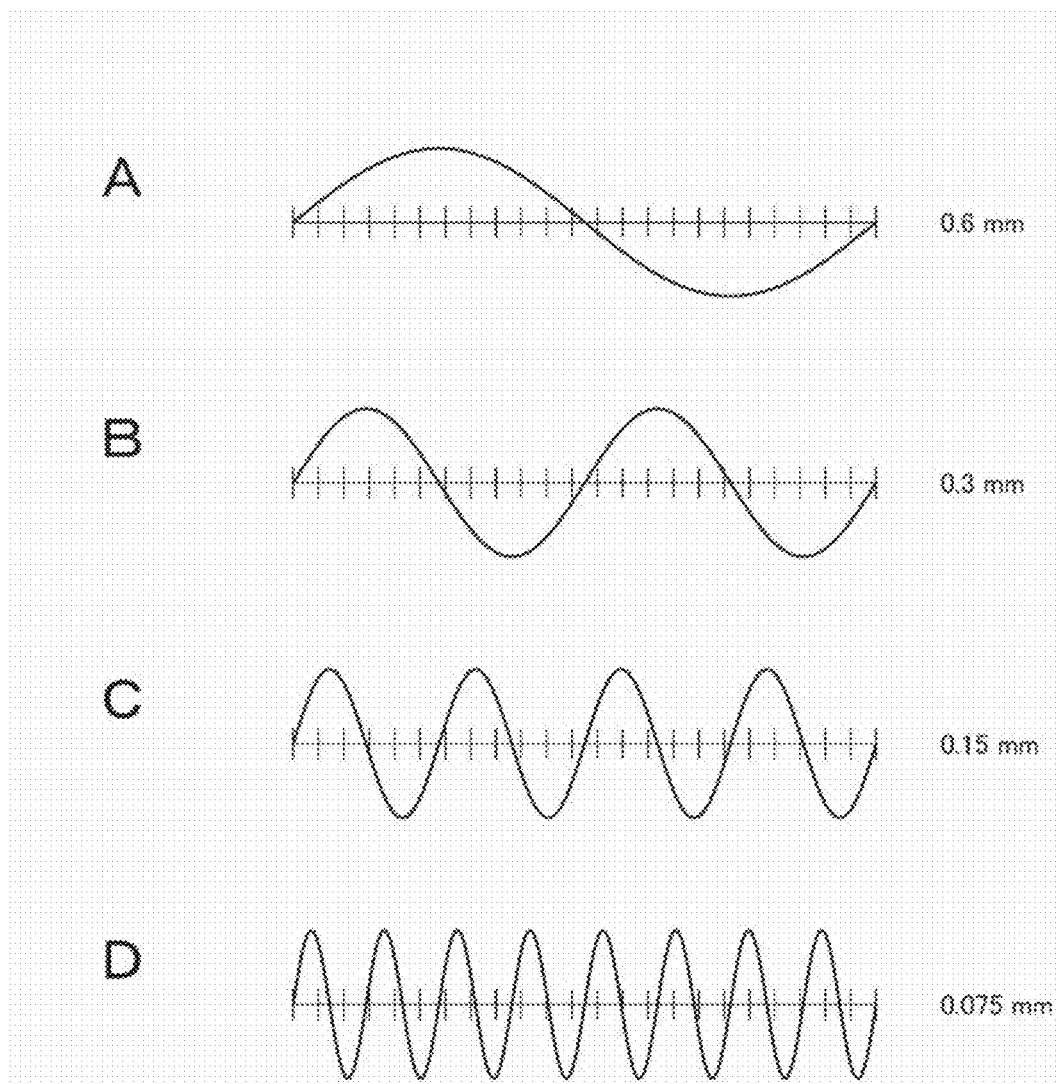
FIGS. 22A to 22D are diagrams for explaining an example of a trigger Q.
Figure 23:
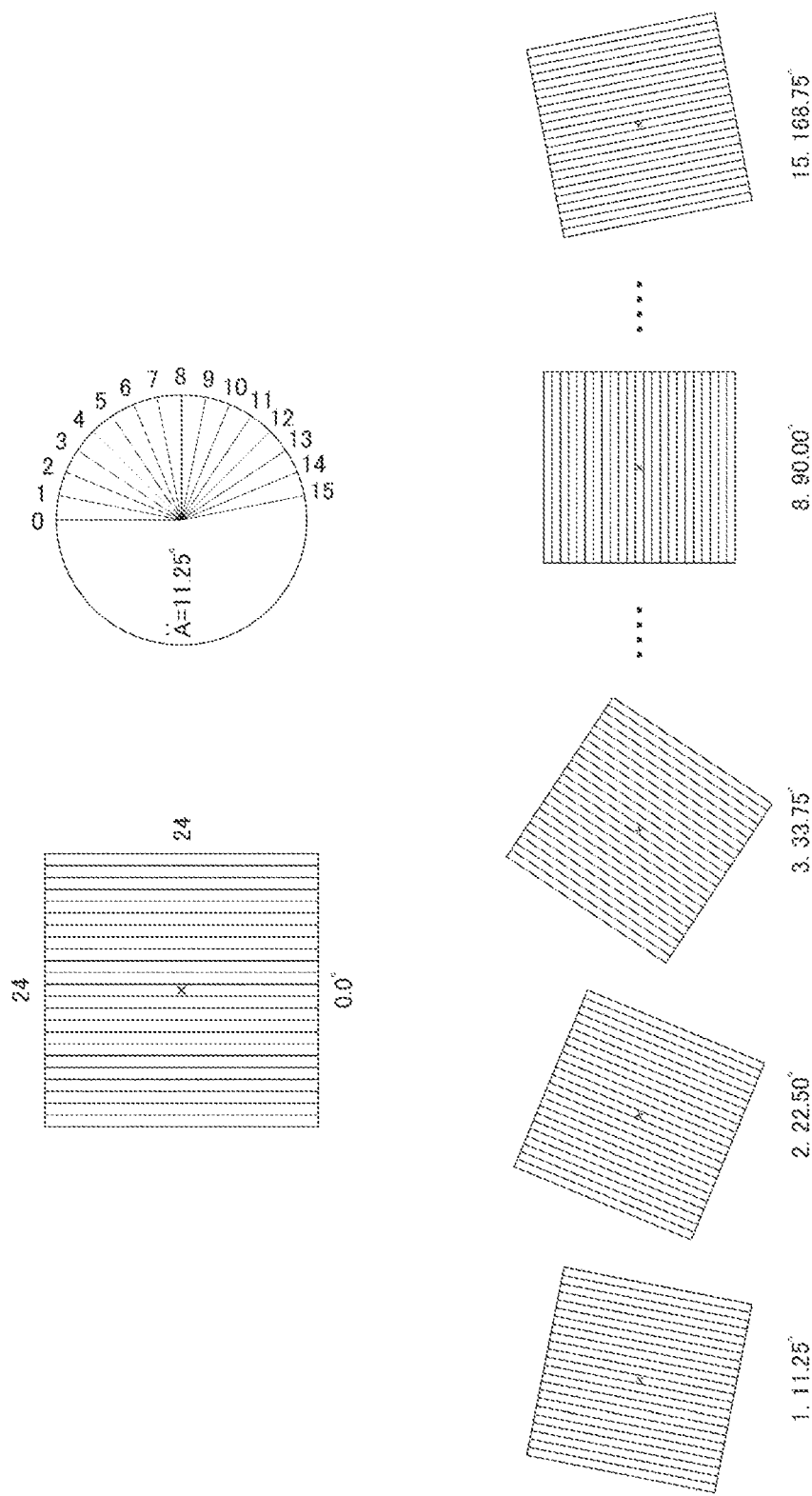
FIG. 23 is a diagram for explaining an example of the trigger Q.

As shown in FIGS. 22A to 22D, a cycle that is conceivable as a cycle of a fingerprint line (in this case, a ridge line and a valley line) of a fingerprint is set. FIG. 22A shows an example of a 0.6 mm-cycle, FIG. 22B shows an example of a 0.3 mm-cycle, FIG. 22C shows an example of a 0.15 mm-cycle, and FIG. 22D shows an example of a 0.075 mm-cycle. A frequency component that corresponds to each cycle is extracted from an image obtained via the imaging element 8. In addition, with respect to each frequency component, for example, responses to 32 (11.25 degree-increments) angle patterns as shown in FIG. 23 are calculated and an average value thereof is obtained. When an average value corresponding to at least one of the four frequency components described above is equal to or greater than a threshold, the possibility that an object appearing in the image is a fingerprint is high. Therefore, a condition requiring that an average value corresponding to at least one of the four frequency components be equal to or greater than the threshold is set as the trigger Q.

Figure 24:
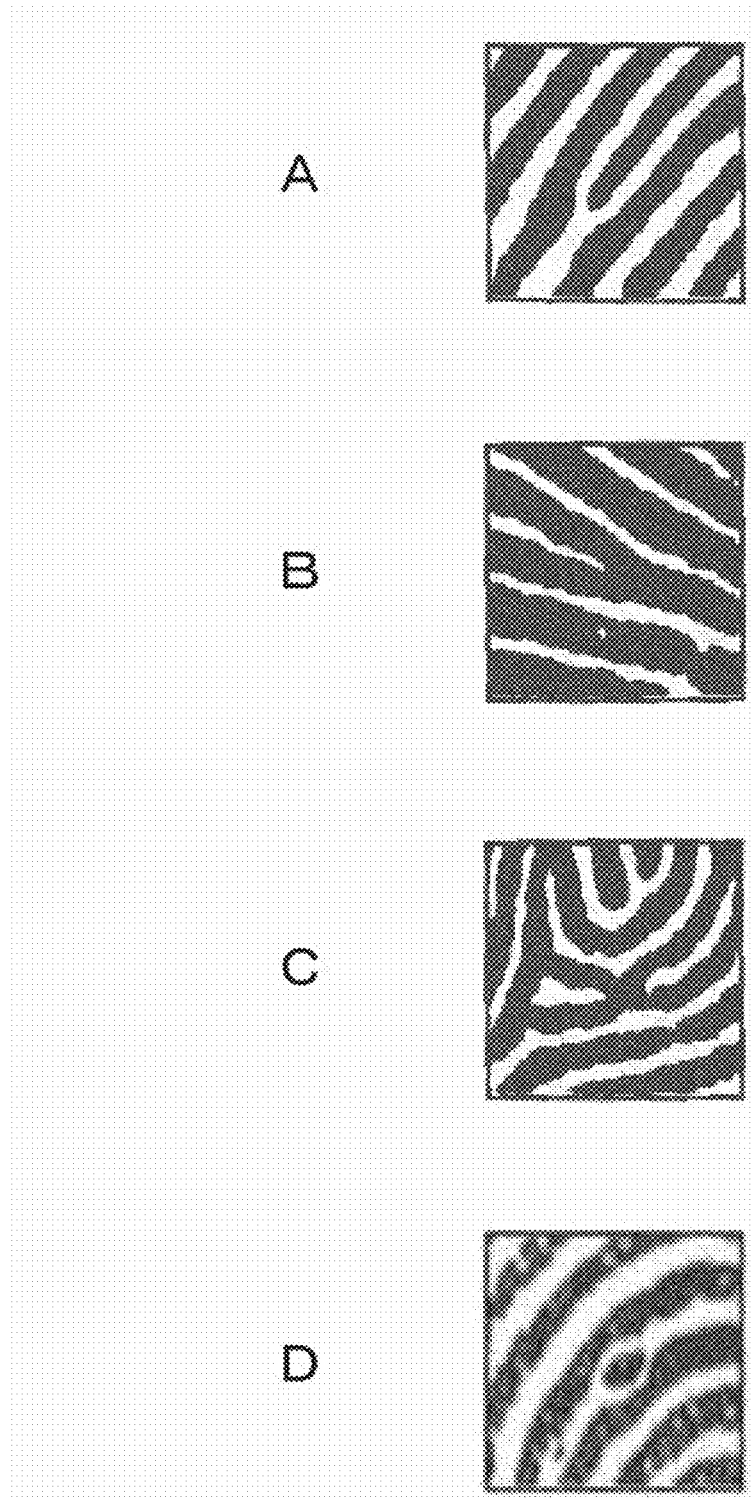
FIGS. 24A to 24D are diagrams to be referred to when explaining another example of the trigger Q.

In addition, a condition requiring that the number of detected feature points of a fingerprint be equal to or greater than a threshold may be set as the trigger Q. In addition to an ending point of a fingerprint line shown in FIG. 24A and a bifurcation of a fingerprint line shown in FIG. 24B, feature points of a fingerprint may include an intersection of fingerprint lines shown in FIG. 24C and isolated points where dots of a fingerprint line shown in FIG. 24D are isolated from each other.

While specific examples of the trigger Q have been described above, the trigger Q is not limited thereto and various conditions may be set as the trigger Q.

[Flow of Processing]

Next, a flow of processing according to the second embodiment will be described with reference to the flow charts shown in FIGS. 25 and 26. Unless otherwise noted, the processing shown in FIGS. 25 and 26 is executed in accordance with, for example, control by the control unit 11.

Figure 25:
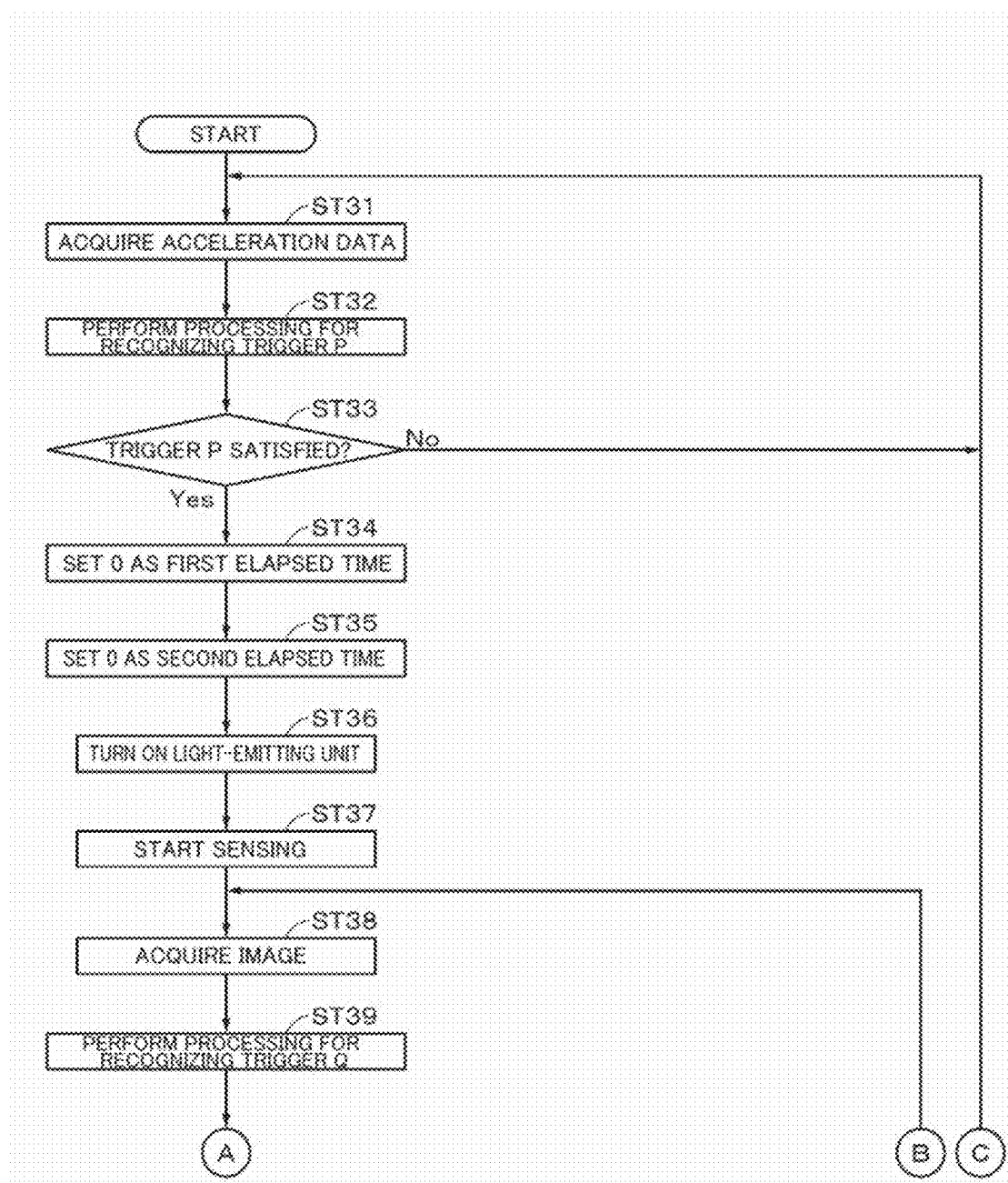
FIG. 25 is a flow chart showing a flow of processing according to a second embodiment.
Figure 26:
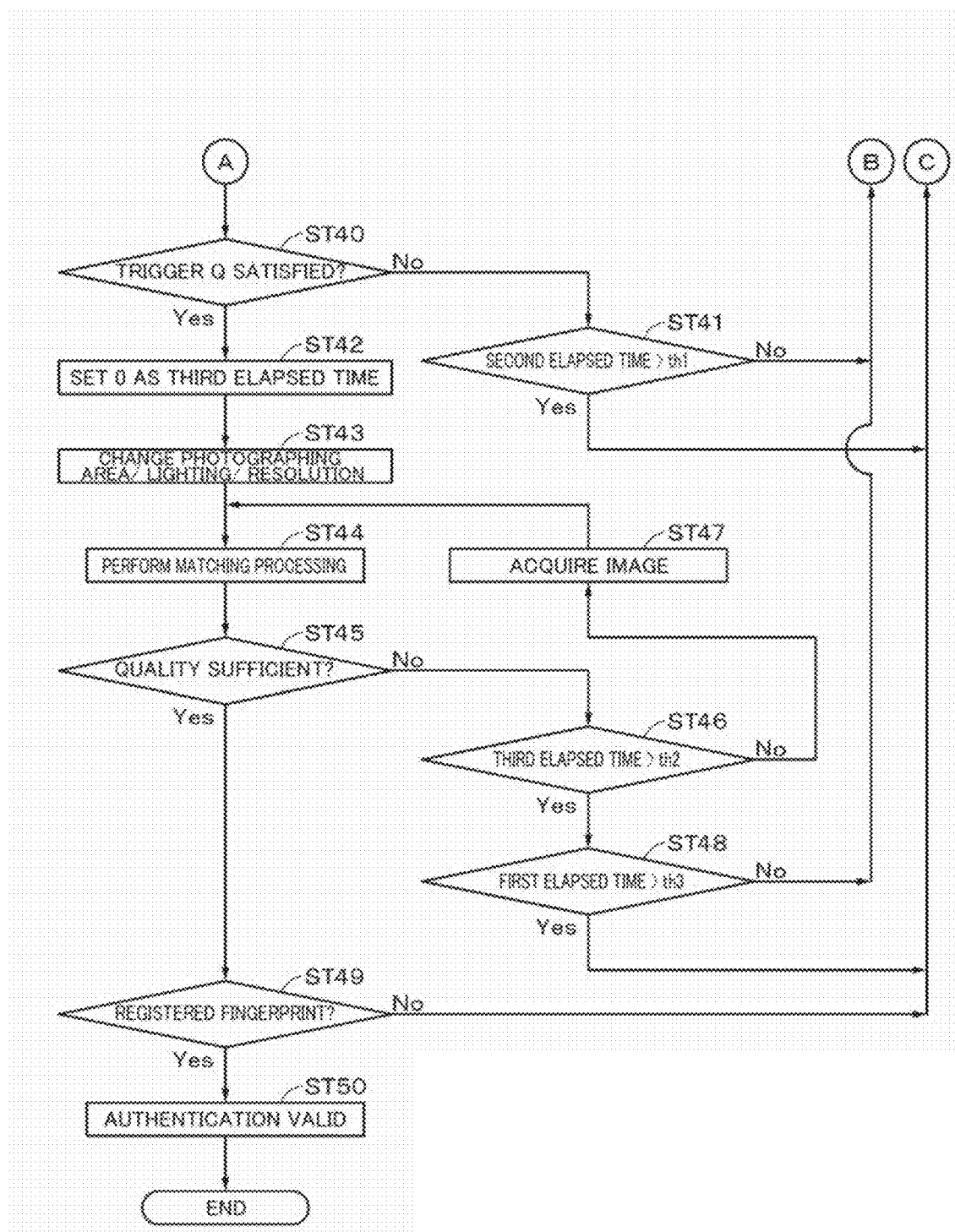
FIG. 26 is a flow chart showing a flow of processing according to the second embodiment.

A, B, and C that are encircled in the flow charts shown in FIGS. 25 and 26 indicate continuity of processing. The following description assumes that the operating mode at the start of processing is mode 0.

In step ST31 shown in FIG. 25, for example, acceleration data is acquired based on, for example, an output of the motion sensor 20. Subsequently, the processing advances to step ST32.

In step ST32, using the acceleration data obtained in step ST31, the control unit 11 performs processing for recognizing whether or not the trigger P is satisfied. As described earlier, whether or not the trigger P is satisfied may be determined using data other than the acceleration data. Subsequently, the processing advances to step ST33.

In step ST33, whether or not the trigger P is satisfied is determined based on a result of processing in step ST32. When the trigger P is not satisfied, the processing returns to step ST31. When the trigger P is satisfied, the processing advances to step ST34.

When the trigger P is satisfied, the operating mode makes a transition from mode 0 to mode 1. In addition, in step ST34, a first elapsed time is set to 0 (initialized). The first elapsed time is a time for determining whether or not processing as a whole has ended within a prescribed time or, in other words, whether or not processing has timed out. Subsequently, the processing advances to step ST35.

In step ST35, a second elapsed time is set to 0 (initialized). The second elapsed time is a time for determining whether or not processing of mode 1 has ended within a prescribed time or, in other words, whether or not processing has timed out. Subsequently, the processing advances to step ST36.

In step ST36, the light-emitting unit 6 is turned on at a brightness corresponding to mode 1. Subsequently, the processing advances to step ST37.

In step ST37, sensing in accordance with a setting corresponding to mode 1 is started. Subsequently, the processing advances to step ST38.

In step ST38, as a result of the sensing in step ST37, an image is acquired via the imaging element 8. Subsequently, the processing advances to step ST39. In step ST39, processing for recognizing the trigger Q is performed. Subsequently, the processing advances to step ST40.

In step ST40 shown in FIG. 26, the control unit 11 determines whether or not the trigger Q is satisfied based on a result of the processing in step ST39. When the trigger Q is not satisfied, the processing advances to step ST41.

In step ST41, a determination is made as to whether or not the second elapsed time is longer than a prescribed threshold th1. For example, th1 is set to around 10 seconds. In this case, when the second elapsed time is longer than the prescribed threshold th1, processing in mode 1 times out and the processing returns to step ST31. When the second elapsed time is equal to or shorter than the prescribed threshold th1, processing in mode 1 is repeated. In other words, the processing returns to step ST38, an image is acquired once again, and processing of step ST38 and thereafter is performed.

In the determination processing in step ST40, when the trigger Q is satisfied, after the operating mode makes a transition from mode 1 to mode 2, the processing advances to step ST42. In step ST42, a third elapsed time is set to 0 (initialized). The third elapsed time is a time for determining whether or not the processing of mode 2 has ended within a prescribed time or, in other words, whether or not the processing has timed out. Subsequently, the processing advances to step ST43.

In step ST43, a setting related to at least one of a photographing area, lighting (the light-emitting unit 6), and resolution in accordance with mode 2 is enabled, photography of an image according to the setting is performed, and a fingerprint image is acquired. In addition, a feature value that characterizes a feature point of the fingerprint image is extracted. Subsequently, the processing advances to step ST44.

In step ST44, matching processing for collating the obtained feature value with a registered feature value is performed. Subsequently, the processing advances to step ST45.

In step ST45, a determination is made as to whether or not quality is sufficient. For example, when the number of detected feature points is equal to or larger than a threshold, quality is determined to be sufficient. In addition, a determination that quality is insufficient may be made when, as a result of the matching processing, the number of feature points determined to be similar based on a comparison of feature values is between a given threshold thA and a given threshold thB (where threshold thA>threshold thB). In this case, when the number of feature points determined to be similar based on a comparison of the feature values is equal to or larger than the threshold thA (in this case, fingerprint authentication is valid) or when the number of feature points determined to be similar based on a comparison of the feature values is equal to or smaller than the threshold thB (in this case, fingerprint authentication is invalid), it is determined that quality for the purpose of determining a result of fingerprint authentication is sufficient. In step ST45, when it is determined that quality is insufficient, the processing advances to step ST46.

In step ST46, a determination is made as to whether or not the third elapsed time is longer than a threshold th2. For example, the threshold th2 is set to around 10 seconds. When the third elapsed time is equal to or shorter than the threshold th2, the processing advances to step ST47.

Since the third elapsed time is equal to or shorter than the threshold th2 and time until a timeout has not elapsed, processing of mode 2 is continued. In other words, in step ST47, an image is acquired once again via the imaging element 8 and processing of step ST44 and thereafter is performed.

When the third elapsed time is longer than the threshold th2, the processing advances to step ST48. In step ST48, a determination is made as to whether or not the first elapsed time is longer than a threshold th3. As a result of the determination, when the first elapsed time is equal to or shorter than the threshold th3, since a time for processing as a whole to time out has not elapsed, the processing returns to step ST38 and processing related to mode 1 is performed once again. As a result of the determination, when the first elapsed time is longer than the threshold th3, since the time for processing as a whole to time out has elapsed, the processing returns to step ST31 that is the first step of processing.

As described above, according to the second embodiment, even when sensing a fingerprint using the imaging element 8, power consumed by the control unit 11 and the imaging element 8 can be suppressed by appropriately setting the operating mode of the wristband-type electronic device 1. In addition, mode transitions can be performed without having to operate an input device.

Modifications of Second Embodiment

While an example in which matching processing related to a fingerprint is not performed in mode 1 has been described in the second embodiment presented above, mode 1 is not limited thereto. For example, matching processing using a low-resolution image may be performed in mode 1. For example, let us assume an application that enables a payment to be made when fingerprint authentication is valid. When a payment amount is, for example, 1000 yen or smaller, a security level need not be set so high. Therefore, processing according to mode 1 is performed and matching processing using a low-resolution image is performed. Conversely, in the case of a large payment amount exceeding 1000 yen, the security level needs to be set high. Therefore, processing according to mode 2 is performed and matching processing using a high-resolution image is performed. In this case, the trigger Q that represents a condition for switching from mode 1 to mode 2 may be a condition in accordance with contents of an application.

Contents of the trigger Q that represents a condition for switching from mode 1 to mode 2 may be dynamically changed. For example, the control unit 11 acquires a remaining capacity of a battery of the wristband-type electronic device 1. When the remaining capacity of the battery or, specifically, an SoC (State of Charge) falls to, for example, 30% or lower, the contents of the trigger Q is switched to more stringent contents (so that a transition of operating modes from mode 1 to mode 2 is less readily made). For example, contents of the trigger Q is set to a combination of the individual examples of the trigger Q described above. According to this processing, even when the remaining capacity of the battery is low, an erroneous transition of the operating mode from mode 1 to mode 2 can be prevented to the greatest extent possible. Therefore, a situation can be prevented where a significant consumption of power by processing related to mode 2 reduces the remaining capacity of the battery and forces the wristband-type electronic device 1 to shut down.

Figure 27:
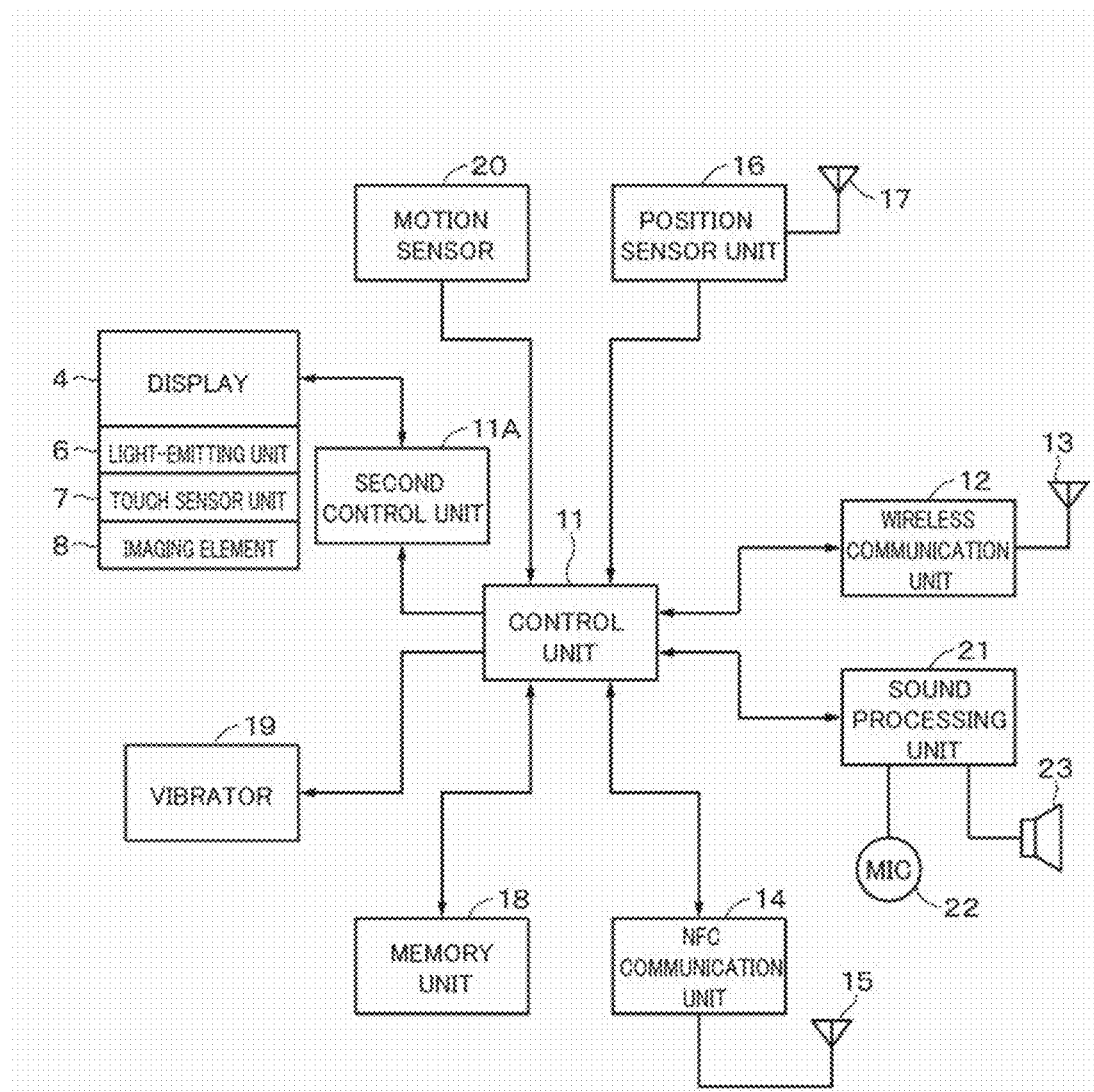
FIG. 27 is a diagram for explaining a modification.

In addition, as shown in FIG. 27, the second embodiment may adopt a configuration in which a control unit (a second control unit 11A) for executing processing related to modes 0 and 1 is provided. Once the trigger Q is satisfied, the second control unit 11A may perform notification processing to the control unit 11 that is a high-order host, and processing such as matching processing related to mode 2 may be performed by the control unit 11. Since the control unit 11 that is the high-order host controls various types of processing by the wristband-type electronic device 1 and, therefore, increases power consumption, when an image is obtained via the imaging element 8 (in other words, when something comes into contact with the display 4), activation of the control unit 11 may cause power consumption as a whole to increase. Therefore, the second control unit 11A that is a low-order control unit for executing mode 0 and mode 1 is preferably provided.

Modifications

While a plurality of embodiments of the present disclosure have been described with specificity above, it is to be understood that the contents of the present disclosure are not limited to the embodiments described above and that various modifications can be made based on the technical ideas of the present disclosure. Hereinafter, modifications will be described.

In the embodiments described above, as a result of matching processing, a threshold that validates fingerprint authentication may be changed in accordance with contents of an application. For example, when fingerprint authentication in order to enable a payment of a large amount is performed, a criterion related to image quality may be raised or a threshold with respect to a collated score may be changed to a larger threshold.

The configuration of the wristband-type electronic device 1 according to the embodiments described above may be modified when appropriate. For example, a configuration from which the light guide plate 5 and the light-emitting unit 6 are omitted may be adopted. In the case of this configuration, for example, photography using light of the display 4 (a specific example is an OLED) is performed.

In the embodiments described above, biological information is not limited to a fingerprint and may be a blood vessel of a hand, capillaries of a retina, or the like, or a combination thereof. It should be noted that a fingerprint need not be a pattern formed by fingerprint lines of an entire fingertip and need only include a part thereof. The same description applies to other types of biological information.

The present disclosure can also be realized by an apparatus, a method, a program, a system, or the like. For example, by making a program that performs the functions described in the embodiments presented above downloadable and having an apparatus that does not include the functions described in the embodiments download and install the program, the controls described in the embodiments can be performed in the apparatus. The present disclosure can also be realized by a server that distributes such a program. In addition, matters described in the respective embodiments and modifications can be combined to the extent feasible.

The present disclosure can also adopt the following configurations.

(1)
An information processing apparatus, including:
a feature point detecting unit configured to detect a feature point from an image including biological information obtained via a sensor unit; and a feature value extracting unit configured to extract a feature value that characterizes the feature point based on a peripheral image including the feature point.

(2)
The information processing apparatus according to (1), including a pre-processing unit configured to perform correction processing with respect to an image that includes the biological information.

(3)
The information processing apparatus according to (2), wherein the pre-processing unit includes a noise removing unit configured to remove noise included in the image.

(4)
The information processing apparatus according to (3), wherein the noise includes noise corresponding to an object other than the biological information.

(5)
The information processing apparatus according to (3) or (4), including a display, wherein
with an operation direction as a reference, the display is arranged on a near side and the sensor unit is arranged on a far side, and
the noise includes noise attributable to a structure of the display.

(6)
The information processing apparatus according to any one of (3) to (5), wherein the sensor unit has a plurality of sub-sensor units, and
the noise includes boundaries of the sub-sensor units.

(7)
The information processing apparatus according to any one of (2) to (6), wherein the pre-processing unit includes an image generating unit configured to generate an image that represents an estimation of a pattern corresponding to the biological information as an image including the biological information.

(8)
The information processing apparatus according to (7), wherein the pattern corresponding to the biological information is a pattern based on a fingerprint line of a fingerprint.

(9)
The information processing apparatus according to (7) or (8), wherein the pre-processing unit includes a certainty map generating unit configured to generate a certainty map that indicates a certainty of a result of the estimation.

(10)
The information processing apparatus according to (9), wherein
an area in which certainty is equal to or higher than a threshold in the image is determined based on a certainty map having been generated by the certainty map generating unit, and
the feature point detecting unit is configured to detect a feature point that is present in the area.

(11)
The information processing apparatus according to any one of (1) to (10), including
a matching processing unit configured to perform matching processing using the feature value and a registered feature value having been registered in advance.

(12)
The information processing apparatus according to any one of (1) to (11), wherein the feature value is stored in a storage unit.

(13)
The information processing apparatus according to any one of (1) to (14), wherein the biological information is a fingerprint.

(14)
The information processing apparatus according to (13), wherein the feature point is at least one of an ending, a bifurcation, an intersection, and an isolated point of a fingerprint line of a fingerprint.

(15)
The information processing apparatus according to (13) or (14), wherein when a sweat gland is present around a feature point, the feature value includes a relative position of the sweat gland with respect to the feature point.

(16)
The information processing apparatus according to (11), wherein a threshold for determining a result of the matching processing is changeable.

(17)
A wearable device, including:
a display with which a fingerprint comes into contact;
a sensor unit configured to acquire an image including a fingerprint; a light-emitting unit configured to emit light at least during acquisition of the image;

a feature point detecting unit configured to detect a feature point from a fingerprint image obtained via the sensor unit; and a feature value extracting unit configured to extract a feature value that characterizes the feature point based on a peripheral image including the feature point.

(18)

An information processing method, including:

by a feature point detecting unit, detecting a feature point from an image including biological information obtained via a sensor unit; and by a feature value extracting unit, extracting a feature value that characterizes the feature point based on a peripheral image including the feature point.

(19)

A program that causes a computer to execute an information processing method including:

by a feature point, detecting unit, detecting a feature point from an image including biological information obtained via a sensor unit; and by a feature value extracting unit, extracting a feature value that characterizes the feature point based on a peripheral image including the feature point.

REFERENCE SIGNS LIST

1 Wearable device
4 Display
6 Light-emitting unit
8 Imaging element
11 Control unit
11A Second control unit
11a Pre-processing unit
11c Feature value extracting unit
11d Matching processing unit
101 Noise removing unit
102 Ridge estimation image generating unit
103 Certainty map generating unit

The invention claimed is:

1. An information processing apparatus, comprising:
a feature point detecting unit configured to detect a feature point from an image including biological information obtained via a sensor; and
a feature value extracting unit configured to extract a feature value that characterizes the feature point based on a peripheral image including the feature point,
wherein the peripheral image includes information on a periphery of the feature point,
wherein the feature value includes at least one frequency of the biological information that is dominant in the peripheral image, and
wherein the feature point detecting unit and the feature value extracting unit are each implemented via at least one processor.

2. The information processing apparatus according to claim 1, further comprising:
a pre-processing unit configured to perform correction processing with respect to the image including the biological information,
wherein the pre-processing unit is implemented via at least one processor.

3. The information processing apparatus according to claim 2,
wherein the pre-processing unit includes a noise removing unit configured to remove noise included in the image.

4. The information processing apparatus according to claim 3,
wherein the noise includes noise corresponding to an object other than the biological information.

5. The information processing apparatus according to claim 3, further comprising:
a display,
wherein with an operation direction as a reference, the display is arranged on a near side and the sensor is arranged on a far side, and
wherein the noise includes noise attributable to a structure of the display.

6. The information processing apparatus according to claim 3,
wherein the sensor has a plurality of sub-sensor units, and
wherein the noise includes boundaries of the sub-sensor units.

7. The information processing apparatus according to claim 2,
wherein the pre-processing unit includes an image generating unit configured to generate an image that represents an estimation of a pattern corresponding to the biological information as the image including the biological information.

8. The information processing apparatus according to claim 7,
wherein the pattern corresponding to the biological information is a pattern based on a fingerprint line of a fingerprint.

9. The information processing apparatus according to claim 7,
wherein the pre-processing unit includes a certainty map generating unit configured to generate a certainty map that indicates a certainty of a result of the estimation.

10. The information processing apparatus according to claim 9,
wherein an area in which certainty is equal to or higher than a threshold in the image is determined based on a certainty map having been generated by the certainty map generating unit, and
wherein the feature point detecting unit is configured to detect a feature point that is present in the area.

11. The information processing apparatus according to claim 1, further comprising:
a matching processing unit configured to perform matching processing using the feature value and a registered feature value having been registered in advance,
wherein the matching processing unit is implemented via at least one processor.

12. The information processing apparatus according to claim 1,
wherein the feature value is stored in a non-transitory computer-readable storage medium.

13. The information processing apparatus according to claim 1,
wherein the biological information is a fingerprint.

14. The information processing apparatus according to claim 13,
wherein the feature point is at least one of an ending, a bifurcation, an intersection, and an isolated point of a fingerprint line of a fingerprint.

15. The information processing apparatus according to claim 13,
wherein when a sweat gland is present around a feature point, the feature value includes a relative position of the sweat gland with respect to the feature point.

16. The information processing apparatus according to claim 11,
wherein a threshold for determining a result of the matching processing is changed based on contents of an application.

17. A wearable device, comprising:
a display with which a fingerprint comes into contact;
a sensor configured to acquire an image including a fingerprint;
a light-emitting unit configured to emit light at least during acquisition of the image;
a feature point detecting unit configured to detect a feature point from a fingerprint image obtained via the sensor; and
a feature value extracting unit configured to extract a feature value that characterizes the feature point based on a peripheral image including the feature point,
wherein the peripheral image includes information on a periphery of the feature point,
wherein the feature value includes at least one frequency of the biological information that is dominant in the peripheral image, and
wherein the light-emitting unit, feature point detecting unit, and the feature value extracting unit are each implemented via at least one processor.

18. An information processing method, comprising:
by a feature point detecting unit, detecting a feature point from an image including biological information obtained via a sensor; and,
by a feature value extracting unit, extracting a feature value that characterizes the feature point based on a peripheral image including the feature point,
wherein the peripheral image includes information on a periphery of the feature point,
wherein the feature value includes at least one frequency of the biological information that is dominant in the peripheral image, and
wherein the feature point detecting unit and the feature value extracting unit are each implemented via at least one processor.

19. A non-transitory computer-readable storage medium having embodied thereon a program, which when executed by a computer causes the computer to execute an information processing method, the information processing method comprising:
by a feature point detecting unit, detecting a feature point from an image including biological information obtained via a sensor; and
by a feature value extracting unit, extracting a feature value that characterizes the feature point based on a peripheral image including the feature point,
wherein the peripheral image includes information on a periphery of the feature point,
wherein the feature value includes at least one frequency of the biological information that is dominant in the peripheral image, and
wherein the feature point detecting unit and the feature value extracting unit are each implemented via at least one processor.

20. The information processing apparatus according to claim 1,
wherein the feature value further includes an angle of the biological information in the peripheral image.

* * * * *